United States Patent
Chen et al.

(10) Patent No.: US 10,155,958 B2
(45) Date of Patent: Dec. 18, 2018

(54) METHOD FOR IMPROVING PLANT RESISTANCE TO INSECTS

(75) Inventors: Xiaoya Chen, Shanghai (CN); Xiuming Wu, Shanghai (CN); Yingbo Mao, Shanghai (CN); Changqing Yang, Shanghai (CN); Lingjian Wang, Shanghai (CN)

(73) Assignees: Shanghai Institutes for Biological Sciences, CAS, Shanghai (CN); Suzhou Kaiyi Biotechnology Co. Ltd., Suzhou, Jiangsu Province (CN)

( * ) Notice: Subject to any disclaimer, the term of this patent is extended or adjusted under 35 U.S.C. 154(b) by 285 days.

(21) Appl. No.: 14/008,436

(22) PCT Filed: Mar. 31, 2012

(86) PCT No.: PCT/CN2012/073409
§ 371 (c)(1),
(2), (4) Date: Nov. 11, 2013

(87) PCT Pub. No.: WO2012/130176
PCT Pub. Date: Oct. 4, 2012

(65) Prior Publication Data
US 2014/0143906 A1 May 22, 2014

(30) Foreign Application Priority Data

Mar. 31, 2011 (CN) .......................... 2011 1 0081074

(51) Int. Cl.
*C12N 15/82* (2006.01)
*C12N 15/113* (2010.01)

(52) U.S. Cl.
CPC ........ *C12N 15/8286* (2013.01); *C12N 15/113* (2013.01); *C12N 15/8218* (2013.01); *Y02A 40/162* (2018.01)

(58) Field of Classification Search
None
See application file for complete search history.

(56) References Cited

U.S. PATENT DOCUMENTS

| 8,872,001 B2* | 10/2014 | Broglie | A01N 57/16 800/301 |
| 8,895,805 B2* | 11/2014 | Chen | C12N 15/8286 536/24.5 |
| 2009/0285784 A1 | 11/2009 | Raemaekers et al. | |
| 2009/0306189 A1 | 12/2009 | Raemaekers et al. | |
| 2010/0050294 A1* | 2/2010 | Chen | C12N 15/8218 800/279 |
| 2017/0114362 A1 | 4/2017 | Baum et al. | |

FOREIGN PATENT DOCUMENTS

| AU | 2006/335978 A1 | 7/2007 |
| CN | 101365795 A | 2/2009 |
| CN | 101851622 A | 10/2010 |
| WO | 2007/080127 A2 | 7/2007 |

OTHER PUBLICATIONS

Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Mao et al (Silencing a cotton bollworm P450 monooxygenase gene by plant-mediated RNAi impairs larval tolerance of gossypol. Nature Biotechnology vol. 25 No. 11 Nov. 2007).*
International Search Report dated Jul. 5, 2012, issued by the State Intellectual Property Office of the Peoples Republic of China in corresponding International Application No. PCT/CN2012/073409, w/ English translation (19 pages).
PCT International Preliminary Report on Patentability dated Mar. 17, 2013, in corresponding International Application No. PCT/CN2012/073409, with English translation (16 pages).
Chen, X. Y., GenBank Acc: EE399600.1 "ha20-1 f05 Helicoverpa armigera midgut Lambda Zap Express Library Helicoverpa armigera cDNA 3—similar to trypsin precursor [Lacanobia oleracea], mRNA sequence"; online, Aug. 15, 2006 (Aug. 15, 2006) (2 pages).
Chen, X. Y., GenBank Acc: EE399464.1, "ha4-1a12 Helicoverpa armigera midgut Lambda Zap Express Library Helicoverpa armigera cDNA 3—similar to dopa decarboxylase [Mamestra brassicae], mRNA sequence", online, Aug. 15, 2006 (Aug. 15, 2006) (2 pages).
Chen, X. Y., GenBank Acc: EE399580.1, "ha20-1a04 Helicoverpa armigera midgut Lambda Zap Express Library Helicoverpa armigera cDNA 3—similar to NADH dehydrogenase (ubiquinone) flavoprotein 2, 24kDa [*Homo sapiens*], RNA sequence", online, Aug. 15, 2006 (Aug. 15, 2006) (2 pages).
Chen, X. Y., GenBank Acc: EE399658.1, "ha2-1d12 Helicoverpa armigera midgut Lambda Zap Express Library Helicoverpa armigera cDNA 3—similar to ATP synthase beta [*Drosophila simulans*], mRNA sequence", online, Aug. 15, 2006 (Aug. 15, 2006) (2 pages).
Chen, X. Y. , GenBank Acc: EE399482.1, "ha4-1h04 Helicoverpa armigera midgut Lambda Zap Express Library Helicoverpa armigera cDNA 3—similar to CG17927-PB, isoform B [*Drosophila melanogaster*], mRNA sequence", online, Aug. 15, 2006 (Aug. 15, 2006) (2 pages).

(Continued)

*Primary Examiner* — Medina A Ibrahim
*Assistant Examiner* — Wayne Zhong
(74) *Attorney, Agent, or Firm* — Osha Liang LLP

(57) ABSTRACT

A method for improving plant insect resistance includes providing target genes derived from insects. Constructs based on the nucleotide sequences of these target genes are designed to form interfering molecules. After being eating by insects, the plant can significantly inhibit expression of corresponding genes in insects. This inhibition is not affected by barrier of the insect digestive systems. The method can improve the insect resistance of plants, reduce pesticide applications, lower the costs of agricultural production, and protect the environment.

9 Claims, 4 Drawing Sheets
Specification includes a Sequence Listing.

(56) References Cited

OTHER PUBLICATIONS

Zhu, X. Y., GenBank Acc: GH999345.1, "ECB-27_M13R_C04_31Mar06 libraries of whol guts from fifth-instar European corn borer larvae *Ostrinia nubilalis* cDNA, mRNA sequence", online, Jul. 16, 2009 (Jul. 16, 2009) (2 pages).

Visser, P.B., et al., GenBank Acc: AF166084.1, "Tobacco rattle virus RNA1 134 kDa protein, 194 kDa protein, 29 kDA protein, and 16 kDa protein genes, complete cds"; https://www.ncbi.nlm.nih.gov/nuccore/AF166084; (Aug. 10, 2017) (4 pages).

Boccara, M., et al., GenBank Acc: X06172.1; "Tobacco rattle virus RNA-1 complete sequence"; https://www.ncbi.nlm.nih.gov/nuccore/X06172.1; (Aug. 7, 2017) (3 pages).

Liu, E., et al.; GenBank Acc: EU165355.1; "Nicotiana benthamiana phytoene desaturase (PDS) mRNA, complete cds"; https://www.ncbi.nlm.nih.gov/nuccore/EU165355.1; (Aug. 7, 2017) (2 pages).

Examination Report (Official Action) dated Mar. 15, 2018, issued by the Intellectual Property Office of India in corresponding Indian Patent Application No. 8195/CHENP/2013, with English translation (7 pages).

\* cited by examiner

SEQUENCE LISTING

```
<160> NUMBER OF SEQ ID NOS: 52

<210> SEQ ID NO 1
<211> LENGTH: 726
<212> TYPE: DNA
<213> ORGANISM: Helicovepa armigera

<400> SEQUENCE: 1
accctactat tgcggctctt ctctacacct ggaactggag cacctactgg caggcttgcg      60
gcggtaccat catcaacaac cgctccattc ttaccgccgc tcactgcacc caaggtgacg     120
cccctggcag atggcgtatc cgtgttggct ccacctgggc aacagcggt ggcgttgtcc     180 acaacgttaa cctgaacatc gtccacccct catacaactc caacactctg aacaatgaca     240
tcgctctcct gcgctccgcc accaccttct ccttcaacaa caacgtgcaa gccgctccca     300
ttgcaggctc caactacaac cttgctgcca accagtttgt ctgggctgct ggatggggca     360
ctatctcctc cggtggtgct gcctccgagc aactccgtca cgtgcagctg attgtcatca     420
accagaacac ttgtgctagc aactacgctt ctgctggtgt caccatcacc aacaacatgt     480
tgtgctccgg ctggaacggc ggtggtcgtg accagtgcca gggagactcc ggcggtcctc     540
tctaccacaa cggcatcgtt gtcggtgtct gctccttcgg tattggatgc ggtctcgcta     600
acttccctgg tgtgaacgct cgcgtatctc agtacacctc ttggatcaac agcaacgctt     660
aagaagtgta atgaggaaat atattgttga tgattttatg atatgcctaa aaaaaaaaaa     720
aaaaaa                                                                 726

<210> SEQ ID NO 2
<211> LENGTH: 1097
<212> TYPE: DNA
<213> ORGANISM: Helicovepa armigera

<400> SEQUENCE: 2
aggccccttg ggcaaaagtg gaacgtgttc cagcatgaac ttgttgcgtg agcccagctt      60
acggatccgc ctcattggct gaatcgtaac tcatgaagcg tgaaagcgga tcttcgattc     120
gatccacaca agtgatgctc gtactcgact gttccgccat gtgagctcaa agaacgcggt     180
ggatcgtcga tgctcaatgt cgatccctgt actgaacacg acagcaggga tcagctccag     240
actaccgtca ctggcaaata ccacttggac gtcgtttcag agcgcttaag ttgtggttcg     300
ttttacgtct gtatggcgtg gagaatctcc agaagcacat cagaaaacac attgcgcttg     360 ccatctatt tgaaaaattg tgcagcgctg acgaaaggtt cgaaatttat gaagaagtga     420
ctatgggact tgtctgcttt agacttaaag gcggtaacga aaagaatgag gaactgctca     480
ggcatataaa tggaagaggc aaaattcatt tagttccttc taagatcgac gacacatact     540
tccttcgatt agcaatttgc tcacgtttca ccgaagatat tgacattcat atatcttggg     600
aggaagtaaa ggctgctgct gatgatgtac ttaaaggtca ctgaatcgct ttgcatttca     660
atataatagc aataattaga gccaaaacat aaattagaca acaatgctgc tactttcttt     720
aaagcaggag agaaacgaga tatttaaaga ttattaaaat ttgatggtat ttattgtatt     780
tagatgcaca gtatatgtaa ctatggtaac tgtgatagaa aaatgtttag taaaagaatt     840
```

```
gtagtgccgt tgtgacaat aaatatctaa ataagatgtc ttctcccgta attatttatt       900
attactgaca ataataaaat gattgttctt tcctatttta gaacaatatt tttgtgttca       960
atgttattta ataatcagtt ttaatgtcac tagattaatt aattttggtt cattaattgt      1020
gtaattatat tcatattata ataatttagc taattaaatg ccgttcgttg cctataaaaa      1080
aacaaaaaaa aaaaaaa                                                     1097

<210> SEQ ID NO 3
<211> LENGTH: 968
<212> TYPE: DNA
<213> ORGANISM: Helicovepa armigera

<400> SEQUENCE: 3
cgctagctga tacgcagctg attacttact aggaacaaag ctgagctcgc cgccctgcag        60
tcgaataggg atcaagaatc gccacgaggg ttgcgacagt gttcgcatat tatttcaata       120
aatctaaaca cagatttgta cattacatgc tttcagctga ggactggagt tcagggcgtg       180
tggcgtgctg catccaggag tattcagacc agctcagctc ttcaacatga cagtctgttc       240
gttcatcgtg atactcctga ggacaaccgt gatatcccgt tcgagttttc agaggccaac       300
aagaagagag tggaagcctt actaggaatc catcctgaag gccacaagcg tggtgccatg       360
atcccactgc tcgacctggc tcagcgtcag gctggaggtt ggctgccgat atctgccatg       420
cataaagtag ctgaaatcct caaacttcct cgcatgagag tttatgaggt tgctacgttc       480
tacactatgt ttattagacg accaatcggc aagtaccata tccaagtttg cacgacaact       540
ccttgctggc tccgaggttc tgatgctatc ctgaaagctc tcactgaggg tacacaatgc       600
catgttggag gaaacagccc ttgtggcaag ttctctatt t ctgaggttga atgccttggt       660
gcctgtgtta atgctcctat gattcaagtc aacgatgatt actacgaaga cctgtcagta       720
gatgacacaa aggaaattat tgaaaagctc aaaagggacg agaaaccgaa agctggccct       780
aggagcggca gattcgcctc agaacccttg ggaggactca cttctctcac cgaagaacct       840
acaggccccg ttttggact acaacccggc ctcaaggcct agaacaaaaa gtttccgttt        900 tgtaaattt t atttataggc aatatttaaa taaatcatgt tagaatcgta aaaaaaaaa       960 aaaaaaaa                                                                968

<210> SEQ ID NO 4
<211> LENGTH: 743
<212> TYPE: DNA
<213> ORGANISM: Helicovepa armigera

<400> SEQUENCE: 4
ataaagtctc acggaggtag caacaggaag aaataaatgg tgggtgcaaa tagtaggcga        60
tgcgtggcct gtgtctgttg tttatgcgaa ttcagcaaca atcaaggccc tgggaaaact       120
taaagaaccc tgcccctgc caccacctcg cccattagac cccacccctt gtactttccc       180
gtgccattgc tgagctagat atctaccttg ctgtgaaccc tctgactccc acatctgtat       240
catgacccaa catatgagct gagcactaca acgttgcccg tggtgtccag aagatctgca       300
ggactacaag tcactccagg acattattgc tatcctgggt atggatgagt tgtctgaaga       360
agataagctg actgtggctc gtgcccgtaa gatccagagg ttcttgtctc agccttttcca       420 ggtggctgag gtgttcactg acatgctgg caaactggtc ccccttgagg aaactatcaa       480
gggcttctct aaaatcctgc agggcgagta tgatcatcta cctgaagtag cgttctacat       540
ggttggaccc attgaggaag ttgtggctaa ggccgaaacc ctggctaagt cgtaaatcac       600
```

| | | |
|---|---|---|
| agggagagag atgttgaggc aggcaccatt ataaatccgt aataagttgt tggcacatgt | 660 | |
| atgcatgagg gagttatgtt atttctaaat aaacttagtg gaaaatatct ataagaaaaa | 720 | |
| aaaaaaatat aaaaaaaaaa aaa | 743 | |

<210> SEQ ID NO 5
<211> LENGTH: 1102
<212> TYPE: DNA
<213> ORGANISM: Helicovepa armigera

<400> SEQUENCE: 5

| | | |
|---|---|---|
| cgaaagctgc gagacctggc atccgtagcc ttgggcgagc ttcaaagagc ttagagactc | 60 | |
| cgaggggaa ggccagaagg gcaatggtga cccgccgtct gcggacgagc tggcggcgaa | 120 | |
| ccaggtcaag cccagaccag gagaaactcc gcaggccttg aacaaacaga ttcaggaact | 180 | |
| gcaggtcagg ctggatgagg cctgaaggcc aaacgcctta agggaggcag gaagggccat | 240 | |
| ccagaaactg gaacagaggg tcagggagct cgagaacgag cttgacggtg aacagaggag | 300 | |
| acacgctgac gcccagaaga acctccgcaa gtccgagagg cgcatcaagg agctcacctt | 360 | |
| tccaggccga ggaggaccgc aagaaccacg agcgcatgca ggacctcgtc gacaaactgc | 420 | |
| aacagaagat caagacctac aagaggcaga tcgaggaagc cgaagaaatc gccgccctca | 480 | |
| acttggctaa gttccgcaag gcacagcagg agttggagga ggccgaggaa agggcagacc | 540 | |
| ttgccgagca ggccatcagc aaattccgtg gcaagggacg tgcgggttcc gctgcgagag | 600 | |
| gagtcagtcc ggcgccccag cgctcgcgtc ccgccttcgc tgacggtttc ggcaccttcc | 660 | |
| caccaaggtt cgacctggcg cccgaagatt tctaaacgtt ccactacaga aaaaaaacgg | 720 | |
| actgtacaga tttttcgttg aaatgtaact aattttttt tatacatagc agttgaaagt | 780 | |
| tacgaatgcg tgaaacgaaa aactgtaaaa aaaaattttg taagccaaca aaaaaaatat | 840 | |
| acactttagt gatctaatct ttttacgaaa ggctattttg taacttgttg atatttattt | 900 | |
| atattattta ttaccgtgga gtatgtatcg agagtgcgag gccgcgagag acgcgcgtga | 960 | |
| gccgcgcgcg cgcatgttcg accgagacac gccccccacc tccgtaccgc cgccggcgcg | 1020 | |
| cgcgcctctc tcgaacgcct cattttgaca tctaataaag cgatatggtt gtcataaaat | 1080 | |
| actaaaaaaa aaaaaaaaaa aa | 1102 | |

<210> SEQ ID NO 6
<211> LENGTH: 128
<212> TYPE: DNA
<213> ORGANISM: Arabidopsis thaliana

<400> SEQUENCE: 6

| | | |
|---|---|---|
| acgttgtaag tctatttttg actcttcttt tttctccgtc acaatttcta cttccaacta | 60 | |
| aaatgctaag aacatggtta taactttttt tttataactt aatatgtgat ttggacccag | 120 | |
| cagataga | 128 | |

<210> SEQ ID NO 7
<211> LENGTH: 28
<212> TYPE: DNA
<213> ORGANISM: artificial sequence
<220> FEATURE:
<223> OTHER INFORMATION: Synthetic

<400> SEQUENCE: 7

| | |
|---|---|
| cgggatccac cctactattg cggctctt | 28 |

<210> SEQ ID NO 8
<211> LENGTH: 26
<212> TYPE: DNA
<213> ORGANISM: artificial sequence
<220> FEATURE:
<223> OTHER INFORMATION: Synthetic

<400> SEQUENCE: 8
cgtctagaag gagcagacac cgacaa                                         26

<210> SEQ ID NO 9
<211> LENGTH: 28
<212> TYPE: DNA
<213> ORGANISM: artificial sequence
<220> FEATURE:
<223> OTHER INFORMATION: Synthetic

<400> SEQUENCE: 9
cggagctcac cctactattg cggctctt                                       28

<210> SEQ ID NO 10
<211> LENGTH: 28
<212> TYPE: DNA
<213> ORGANISM: artificial sequence
<220> FEATURE:
<223> OTHER INFORMATION: Synthetic

<400> SEQUENCE: 10
cggcggccgc aggagcagac accgacaa                                       28

<210> SEQ ID NO 11
<211> LENGTH: 26
<212> TYPE: DNA
<213> ORGANISM: artificial sequence
<220> FEATURE:
<223> OTHER INFORMATION: Synthetic

<400> SEQUENCE: 11
cgggatcctg tatggcgtgg agaatc                                         26

<210> SEQ ID NO 12
<211> LENGTH: 26
<212> TYPE: DNA
<213> ORGANISM: artificial sequence
<220> FEATURE:
<223> OTHER INFORMATION: Synthetic

<400> SEQUENCE: 12
cgtctagaca gcagcagcct ttactt                                         26

<210> SEQ ID NO 13
<211> LENGTH: 26
<212> TYPE: DNA
<213> ORGANISM: artificial sequence
<220> FEATURE:
<223> OTHER INFORMATION: Synthetic

<400> SEQUENCE: 13
cggagctctg tatggcgtgg agaatc                                         26

<210> SEQ ID NO 14
<211> LENGTH: 28
<212> TYPE: DNA
<213> ORGANISM: artificial sequence
<220> FEATURE:
<223> OTHER INFORMATION: Synthetic

<400> SEQUENCE: 14
cggcggccgc cagcagcagc ctttactt                                                28

<210> SEQ ID NO 15
<211> LENGTH: 29
<212> TYPE: DNA
<213> ORGANISM: artificial sequence
<220> FEATURE:
<223> OTHER INFORMATION: Synthetic

<400> SEQUENCE: 15
cgggatccca acaagaagag agtggaagc                                               29

<210> SEQ ID NO 16
<211> LENGTH: 26
<212> TYPE: DNA
<213> ORGANISM: artificial sequence
<220> FEATURE:
<223> OTHER INFORMATION: Synthetic

<400> SEQUENCE: 16
cgtctagatt tcggtttctc gtccct                                                  26

<210> SEQ ID NO 17
<211> LENGTH: 29
<212> TYPE: DNA
<213> ORGANISM: artificial sequence
<220> FEATURE:
<223> OTHER INFORMATION: Synthetic

<400> SEQUENCE: 17
cggagctcca acaagaagag agtggaagc                                               29

<210> SEQ ID NO 18
<211> LENGTH: 28
<212> TYPE: DNA
<213> ORGANISM: artificial sequence
<220> FEATURE:
<223> OTHER INFORMATION: Synthetic

<400> SEQUENCE: 18
cggcggccgc tttcggtttc tcgtccct                                                28

<210> SEQ ID NO 19
<211> LENGTH: 26
<212> TYPE: DNA
<213> ORGANISM: artificial sequence
<220> FEATURE:
<223> OTHER INFORMATION: Synthetic

<400> SEQUENCE: 19
cgggatccga ggaccgcaag aaccac                                                  26

<210> SEQ ID NO 20
<211> LENGTH: 24
<212> TYPE: DNA
<213> ORGANISM: artificial sequence
<220> FEATURE:
<223> OTHER INFORMATION: Synthetic

<400> SEQUENCE: 20
cgtctagatg ggaaggtgcc gaaa                                                    24

-continued

```
<210> SEQ ID NO 21
<211> LENGTH: 26
<212> TYPE: DNA
<213> ORGANISM: artificial sequence
<220> FEATURE:
<223> OTHER INFORMATION: Synthetic

<400> SEQUENCE: 21
cggagctcga ggaccgcaag aaccac                                      26

<210> SEQ ID NO 22
<211> LENGTH: 26
<212> TYPE: DNA
<213> ORGANISM: artificial sequence
<220> FEATURE:
<223> OTHER INFORMATION: Synthetic

<400> SEQUENCE: 22
cggcggccgc tgggaaggtg ccgaaa                                      26

<210> SEQ ID NO 23
<211> LENGTH: 28
<212> TYPE: DNA
<213> ORGANISM: artificial sequence
<220> FEATURE:
<223> OTHER INFORMATION: Synthetic

<400> SEQUENCE: 23
cgggatccct accttgctgt gaaccctc                                    28

<210> SEQ ID NO 24
<211> LENGTH: 26
<212> TYPE: DNA
<213> ORGANISM: artificial sequence
<220> FEATURE:
<223> OTHER INFORMATION: Synthetic

<400> SEQUENCE: 24
cgtctagaaa tggtgcctgc ctcaac                                      26

<210> SEQ ID NO 25
<211> LENGTH: 28
<212> TYPE: DNA
<213> ORGANISM: artificial sequence
<220> FEATURE:
<223> OTHER INFORMATION: Synthetic

<400> SEQUENCE: 25
cggagctcct accttgctgt gaaccctc                                    28

<210> SEQ ID NO 26
<211> LENGTH: 28
<212> TYPE: DNA
<213> ORGANISM: artificial sequence
<220> FEATURE:
<223> OTHER INFORMATION: Synthetic

<400> SEQUENCE: 26
cggcggccgc aatggtgcct gcctcaac                                    28

<210> SEQ ID NO 27
<211> LENGTH: 26
<212> TYPE: DNA
<213> ORGANISM: artificial sequence
<220> FEATURE:
<223> OTHER INFORMATION: Synthetic
```

```
<400> SEQUENCE: 27
tctagaacgt tgtaagtcta tttttg                                          26

<210> SEQ ID NO 28
<211> LENGTH: 28
<212> TYPE: DNA
<213> ORGANISM: artificial sequence
<220> FEATURE:
<223> OTHER INFORMATION: Synthetic

<400> SEQUENCE: 28
gcggccgctc tgctgggtcc aaatcaca                                        28

<210> SEQ ID NO 29
<211> LENGTH: 20
<212> TYPE: DNA
<213> ORGANISM: artificial sequence
<220> FEATURE:
<223> OTHER INFORMATION: Synthetic

<400> SEQUENCE: 29
accctactat tgcggctctt                                                 20

<210> SEQ ID NO 30
<211> LENGTH: 18
<212> TYPE: DNA
<213> ORGANISM: artificial sequence
<220> FEATURE:
<223> OTHER INFORMATION: Synthetic

<400> SEQUENCE: 30
aggagcagac accgacaa                                                   18

<210> SEQ ID NO 31
<211> LENGTH: 18
<212> TYPE: DNA
<213> ORGANISM: artificial sequence
<220> FEATURE:
<223> OTHER INFORMATION: Synthetic

<400> SEQUENCE: 31
tgtatggcgt ggagaatc                                                   18

<210> SEQ ID NO 32
<211> LENGTH: 18
<212> TYPE: DNA
<213> ORGANISM: artificial sequence
<220> FEATURE:
<223> OTHER INFORMATION: Synthetic

<400> SEQUENCE: 32
cagcagcagc ctttactt                                                   18

<210> SEQ ID NO 33
<211> LENGTH: 21
<212> TYPE: DNA
<213> ORGANISM: artificial sequence
<220> FEATURE:
<223> OTHER INFORMATION: Synthetic

<400> SEQUENCE: 33
caacaagaag agagtggaag c                                               21
```

```
<210> SEQ ID NO 34
<211> LENGTH: 18
<212> TYPE: DNA
<213> ORGANISM: artificial sequence
<220> FEATURE:
<223> OTHER INFORMATION: Synthetic

<400> SEQUENCE: 34
tttcggtttc tcgtccct                                                 18

<210> SEQ ID NO 35
<211> LENGTH: 20
<212> TYPE: DNA
<213> ORGANISM: artificial sequence
<220> FEATURE:
<223> OTHER INFORMATION: Synthetic

<400> SEQUENCE: 35
ctaccttgct gtgaaccctc                                               20

<210> SEQ ID NO 36
<211> LENGTH: 18
<212> TYPE: DNA
<213> ORGANISM: artificial sequence
<220> FEATURE:
<223> OTHER INFORMATION: Synthetic

<400> SEQUENCE: 36
aatggtgcct gcctcaac                                                 18

<210> SEQ ID NO 37
<211> LENGTH: 18
<212> TYPE: DNA
<213> ORGANISM: artificial sequence
<220> FEATURE:
<223> OTHER INFORMATION: Synthetic

<400> SEQUENCE: 37
gaggaccgca agaaccac                                                 18

<210> SEQ ID NO 38
<211> LENGTH: 16
<212> TYPE: DNA
<213> ORGANISM: artificial sequence
<220> FEATURE:
<223> OTHER INFORMATION: Synthetic

<400> SEQUENCE: 38
tgggaaggtg ccgaaa                                                   16

<210> SEQ ID NO 39
<211> LENGTH: 20
<212> TYPE: DNA
<213> ORGANISM: artificial sequence
<220> FEATURE:
<223> OTHER INFORMATION: Synthetic

<400> SEQUENCE: 39
accaatcggc aagtaccata                                               20

<210> SEQ ID NO 40
<211> LENGTH: 22
<212> TYPE: DNA
<213> ORGANISM: artificial sequence
<220> FEATURE:
<223> OTHER INFORMATION: Synthetic
```

```
<400> SEQUENCE: 40
aacggaaact ttttgttcta gg                                                22

<210> SEQ ID NO 41
<211> LENGTH: 20
<212> TYPE: DNA
<213> ORGANISM: artificial sequence
<220> FEATURE:
<223> OTHER INFORMATION: Synthetic

<400> SEQUENCE: 41
ctagcaattt atcccgaagg                                                   20

<210> SEQ ID NO 42
<211> LENGTH: 22
<212> TYPE: DNA
<213> ORGANISM: artificial sequence
<220> FEATURE:
<223> OTHER INFORMATION: Synthetic

<400> SEQUENCE: 42
caggtcctca taatagtcat cg                                                22

<210> SEQ ID NO 43
<211> LENGTH: 27
<212> TYPE: DNA
<213> ORGANISM: artificial sequence
<220> FEATURE:
<223> OTHER INFORMATION: Synthetic

<400> SEQUENCE: 43
cttgaagaag aagactttcg aagtctc                                           27

<210> SEQ ID NO 44
<211> LENGTH: 18
<212> TYPE: DNA
<213> ORGANISM: artificial sequence
<220> FEATURE:
<223> OTHER INFORMATION: Synthetic

<400> SEQUENCE: 44
caacccacct tccagaca                                                     18

<210> SEQ ID NO 45
<211> LENGTH: 870
<212> TYPE: DNA
<213> ORGANISM: Ostrinia nubilalis

<400> SEQUENCE: 45
gcacgaggcg cttgttcgcg aacagtgttt cgcaataact tttataaaaa ttacaagaaa        60
acaacagtaa atcatgttgt ccagcctcag aactggagtt cagggcttgt ggcgcactac       120
ttccagggcc ctgcagacca gctcgaccct gcaacatgac agtcttttcg tccaccgaga       180
cacccctgag gacaaccctc acataccgtt cgagtttacc ccacagaacc aaaagagggt       240
ggaagcactc ctagcaattt atcccgaagg acacaagaga ggtgccatga ttcctctact       300
ggacttggcc cagcgtcagg caggaggctg gctgccaatc tccgcgatgc acaaagtagc       360
ggaagtcctc aatttacctc gcatgagagt ctacgaagta gctacattct acaccatgtt       420
tattaggaga ccaataggca aataccacgt ccaagtgtgc acaaccactc cttgctggct       480
gaggggctcg gacgctgtgc tgaacgctat caaggaagca actggctgtg aagttggagg       540
caacagccct tgcggaaaat tctccatttc tgaggttgaa tgtcttggag cctgtgtcaa       600
```

| | |
|---|---|
| cgcaccaatg attcaagtta acgatgacta ttatgaggac ctgtccgttg aagacacaaa | 660 |
| ggaaattatc gaaaagctaa agaaagacga aaaaccatta ccgggtccca gaagcggcag | 720 |
| gttcgcatcc gagcctctgg gagggctcac gtccctcacg gaagaaccca cgggccccgg | 780 |
| cttcggcgta caagacgccc tgaaggccta ggcagatgta cattgttttg taattttatt | 840 |
| tcataggtat ttaataaatc atgttagatc | 870 |

<210> SEQ ID NO 46
<211> LENGTH: 758
<212> TYPE: DNA
<213> ORGANISM: tobacco

<400> SEQUENCE: 46

| | |
|---|---|
| tggaagacaa gtcattggtc accttgaaga agaagacttt cgaagtctca aaattctcaa | 60 |
| atctaggggc cattgaattg tttgtggacg gtaggaggaa gagaccgaag tattttcaca | 120 |
| gaagaagaga aactgtccta aatcatgttg gtgggaagaa gagtgaacac aagttagacg | 180 |
| tttttgacca aagggattac aaaatgatta aatcttacgc gtttctaaag atagtaggtg | 240 |
| tacaactagt tgtaacatca catctacctg cagatacgcc tgggttcatt caaatcgatc | 300 |
| tgttggattc gagacttact gagaaaagaa agagaggaaa gactattcag agattcaaag | 360 |
| ctcgagcttg cgataactgt tcagttgcgc agtacaaggt tgaatacagt atttccacac | 420 |
| aggagaacgt acttgatgtc tggaaggtgg gttgtatttc tgagggcgtt ccggtctgtg | 480 |
| acggtacata ccctttcagt atcgaagtgt cgctaatatg ggttgctact gattcgacta | 540 |
| ggcgcctcaa tgtggaagaa ctgaacagtt cggattacat tgaaggcgat tttaccgatc | 600 |
| aagaggtttt cggtgagttc atgtctttga acaagtgga gatgaagacg attgaggcga | 660 |
| agtacgatgg tccttacaga ccagctacta ctagacctaa gtcattattg tcaagtgaag | 720 |
| atgttaagag agcgtctaat aagaaaaact cgtcttaa | 758 |

<210> SEQ ID NO 47
<211> LENGTH: 28
<212> TYPE: DNA
<213> ORGANISM: artificial sequence
<220> FEATURE:
<223> OTHER INFORMATION: Synthetic

<400> SEQUENCE: 47

| | |
|---|---|
| cgggatccac caatcggcaa gtaccata | 28 |

<210> SEQ ID NO 48
<211> LENGTH: 30
<212> TYPE: DNA
<213> ORGANISM: artificial sequence
<220> FEATURE:
<223> OTHER INFORMATION: Synthetic

<400> SEQUENCE: 48

| | |
|---|---|
| cgtctagaaa cggaaacttt ttgttctagg | 30 |

<210> SEQ ID NO 49
<211> LENGTH: 28
<212> TYPE: DNA
<213> ORGANISM: artificial sequence
<220> FEATURE:
<223> OTHER INFORMATION: Synthetic

<400> SEQUENCE: 49

| | |
|---|---|
| cgggatccct agcaatttat cccgaagg | 28 |

```
<210> SEQ ID NO 50
<211> LENGTH: 30
<212> TYPE: DNA
<213> ORGANISM: artificial sequence
<220> FEATURE:
<223> OTHER INFORMATION: Synthetic

<400> SEQUENCE: 50
cgtctagaca ggtcctcata atagtcatcg                                        30

<210> SEQ ID NO 51
<211> LENGTH: 28
<212> TYPE: DNA
<213> ORGANISM: artificial sequence
<220> FEATURE:
<223> OTHER INFORMATION: Synthetic

<400> SEQUENCE: 51
cgggatccac caatcggcaa gtaccata                                          28

<210> SEQ ID NO 52
<211> LENGTH: 30
<212> TYPE: DNA
<213> ORGANISM: artificial sequence
<220> FEATURE:
<223> OTHER INFORMATION: Synthetic

<400> SEQUENCE: 52
cgtctagaaa cggaaacttt ttgttctagg                                        30
```

METHOD FOR IMPROVING PLANT RESISTANCE TO INSECTS

CROSS REFERENCE TO RELATED APPLICATIONS

This is a national stage application based on PCT/CN2012/073409, filed on Mar. 31, 2012, which claims priority to Chinese Patent Application No. CN 201110081074.9, filed on Mar. 31, 2011. This application claims the priority of these prior applications and incorporates their disclosures by reference in their entireties.

TECHNICAL FIELD

The present invention relates to plant biotechnology and plant improvement via genetic engineering. Particularly, the present invention relates to new target genes in insects, and there expression can be specifically suppressed in insects through plant-mediated RNAi technique, thereby suppress insect growth and improve insect resistance of plants. The invention discloses the sequences of these target genes and their applications in the area of RNAi-mediated insect resistance in transgenic plants.

BACKGROUND OF THE INVENTION

In agricultural productions, damages caused by pests have always been an important factor that influences the agricultural outputs. Every year, a large sum of human and material resources are consumed to reduce damages caused by pests in order to improve crop yields. However, wide spread applications of agriculture chemicals result in serious environmental contamination and cause severe damages to biodiversity in farms. Residual pesticides in farm products are also an important factor threatening human health. At the same time, long-term use of pesticides increases their resistance to the pesticides, resulting in ever increasing dosages of pesticides and changing the types of pesticides. This further exacerbates the environmental problems. In consideration of environmental protection and sustainable development, new methods for fighting pests are urgently needed.

Inserting insect-resistant genes, such as the Bt gene, into plants to produce insecticidal proteins in the plants can significantly improve plants' resistance to insects or pests. At the same time, this can reduce the applications of pesticides. At present, insect-resistant transgenic soybeans, Bt cotton, etc., have been widely cultivated, leading to great economic and social benefits. However, insect resistances against these proteins have been observed, and performances of these transgenic crops are also decreased. In addition, exclusively suppressing one specific insect can also lead to the boosts of other insects. Therefore, it is necessary to develop new insect-resistant transgenic plants in order to effectively and/or specifically counter the damages caused by pests.

SUMMARY OF THE INVENTION

The present invention aims to provide a method for enhancing insect resistance of plants.

The first aspect of the invention relates to methods for enhancing insect resistance of plants. A method comprises the following steps: expressing an interfering molecule that specifically interferes with the expression of an above-described insect gene (or its fragments) in a plant.

Said insect gene may be selected from trypsin gene, dopa decarboxylase gene, NADH dehydrogenase flavoprotein 2 gene, ATP synthase beta subunit gene, myosin heavy chain B isoform gene.

In another preferred embodiment, after feeding on the plants (transgenic plants), the genes or their fragments in insects will be down-regulated or silenced, thereby the growth or development of the insects will be inhibited or the insects will die.

In another preferred embodiment, said interfering molecules may be selected from (but not limited to), a dsRNA, an antisense nucleic acid (nucleotide), a small interfering RNA (siRNA) or miRNA targeting said insect gene or its fragment or a transcript thereof for inhibiting or silencing that target gene.

In another preferred embodiment, said method comprises:

(1) providing a construct, said construct comprises the following structure:

$$\text{Seq}_{sense}\text{-X-Seq}_{antisense}; \quad \text{Formula I}$$

wherein, $\text{Seq}_{sense}$ is a nucleotide sequence from said insect gene or its fragment, and the nucleotide sequences of $\text{Seq}_{sense}$ and $\text{Seq}_{antisense}$ are basically complementary with each other.

X is an intervening sequence between $\text{Seq}_{sense}$ and $\text{Seq}_{antisense}$, and said intervening sequence is not complementary with the sequences of $\text{Seq}_{sense}$ and $\text{Seq}_{antisense}$.

(2) transforming a plant with the construct of (1).

In another preferred embodiment, the length of said intervening sequence is 30-300 nt; preferably is 50-200 nt; more preferably is 100-150 nt.

In another preferred embodiment, length of said $\text{Seq}_{sense}$ or $\text{Seq}_{antisense}$ is at least 18 bp, preferably is at least 20 bp; more preferably is at least 50 bp; more preferably is at least 100 bp; more preferably is 100-700 bp; and more preferably is 200-600 bp.

In another preferred embodiment, after transforming said construct into a plant, said construct expresses in a plant cell, tissue or organ to produce an interfering molecule shown in formula II.

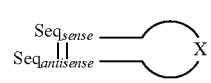

Formula II

In that formula, $\text{Seq}_{sense}$, $\text{Seq}_{antisense}$ and X are as define above, $\parallel$ represents hydrogen bonds formed between $\text{Seq}_{sense}$ and $\text{Seq}_{antisense}$.

In another preferred embodiment, step (2) comprises:

(a) providing *Agrobacterium tumefaciens* carrying an expression vector, said expression vector contains the construct described in (1);

(b) contacting a plant cell, tissue, or organ with the *Agrobacterium tumefaciens* described in step (a) to transfect said construct into the plant cell, tissue, or organ.

In another preferred embodiment, said method further comprises:

(c) selecting the plant cell, tissue, or organ that has been transformed with said construct.

(d) regenerating a plant from the plant cell, tissue, or organ described in step (c).

In another preferred embodiment, said construct is in an expression vector.

In another preferred embodiment, said expression vector further comprises one or more operably linked elements, such as promoter, terminator, etc., which can be transcribed in a plant.

In another preferred embodiment, said Seq$_{sense}$ is selected form:

SEQ ID NO: 1 (trypsin precursor, trypsin precursor gene of *Helicoverpa armigera*) or a sequence corresponding to positions 1th-576th thereof;

SEQ ID NO: 2 (dopa decarboxylase, dopa decarboxylase gene of *Helicoverpa armigera*) or a sequence corresponding to positions 311th-621th thereof;

SEQ ID NO: 3 (NADH dehydrogenase ubiquinone flavoprotein, NADH dehydrogenase ubiquinone flavoprotein 2 gene of *Helicoverpa armigera*) or a sequence corresponding to positions 297th-771th or positions 501th-899th thereof;

SEQ ID NO: 4 (ATP synthase beta, ATP synthase beta subunit gene of *Helicoverpa armigera*) or a sequence corresponding to positions 203th-630th thereof;

SEQ ID NO: 5 (Myosin heavy chain, isoform B, Myosin heavy chain, isoform B gene of *Helicoverpa armigera*) or a sequence corresponding to positions 372th-662th thereof; or SEQ ID NO: 45 (NADH dehydrogenase ubiquinone flavoprotein 2 gene of *Ostrinia nubilalis*, NADH dehydrogenase ubiquinone flavoprotein 2) or a sequence corresponding to positions 251th-643th thereof.

In another preferred embodiment, said plant may be selected from: dicotyledon, monocotyledon, or gymnosperm.

In another preferred embodiment, said monocotyledon may be selected from: corn, rice, wheat, barley, sorghum, etc.

In another preferred embodiment, wherein the dicotyledon is selected from: Brassicaceae, Malvaceae, Solanaceae, etc.

In another preferred embodiment, said dicotyledon is selected from: cotton, soybean, rapeseed, peanut, etc.

In another preferred embodiment, said insect is selected from: phytophagous insects.

In another preferred embodiment, the phytophagous insects are Lepidoptera, Homoptera insects, Collembola, Isoptera insects, Coleoptera, Diptera, Hymenoptera insects, Orthoptera insects, Hemiptera, or Thysanoptera insects.

In another preferred embodiment, the phytophagous insect is cotton bollworm (*Helicoverpa armigera*), corn borer, aphids, planthoppers, or soybean borer.

In another preferred embodiment, said insect gene is a cotton bollworm (*Helicoverpa armigera*) gene, corn borer gene, aphids gene, or planthoppers gene.

In another preferred embodiment, for the control of an insect (such as *Helicoverpa armigera*), an interfering molecule that can specifically interfere with the expression of an insect gene (such as a gene from *Helicoverpa armigera*) is expressed in a plant. Because the genes of phytophagous insects are highly homologous, the same genes from different insects (such as the same ATP synthase genes) usually have the same conserved positions (if the sequence is long enough). Therefore, in another preferred embodiment, for the control of an insect, an interfering molecule that can specifically interfere with the expression of an insect gene is expressed in a plant, wherein the interfering molecule is derived from a gene from a non-target insect that is different from the insect being targeted (and the target insect contains a homologous gene that is highly homologous with the gene in the non-target insect).

In another aspect of the invention, it provides a method for producing transgenic plants, said transgenic plants have improved insect resistance. The method comprises expressing in a plant an interfering molecule that can specifically interfere with the expression of an insect gene;

Said insect genes are selected from trypsin precursor gene, dopa decarboxylase gene, NADH dehydrogenase ubiquinone flavoprotein 2 gene, ATP synthase beta subunit gene, or myosin heavy chain isoform B gene.

In another aspect of the invention, it provides plants with increased insect resistance, which is produced by the methods described above.

In another aspect of the invention, it provides uses of insect genes or their fragments, which are used as targets for preparing interfering molecules that can specifically inhibit or silence the expression of genes in insects. The insect genes may be selected from trypsin precursor gene, dopa decarboxylase gene, NADH dehydrogenase ubiquinone flavoprotein 2 gene, ATP synthase beta subunit gene, or myosin heavy chain isoform B gene.

In another preferred embodiment, said insect gene is from cotton bollworm (*Helicoverpa armigera*), corn borer, Aphid, or planthopper.

In another aspect of the invention, it provides a construct. The construct comprises the following structure:

$$Seq_{sense}\text{-X-}Seq_{antisense};$$

Wherein Seq$_{sense}$ is a nucleotide sequence from said insect gene or its fragment. The nucleotide sequences of Seq$_{sense}$ and Seq$_{antisense}$ are basically complementary to each other;

X is an intervening sequence between Seq$_{sense}$ and Seq$_{antisense}$, and said intervening sequence is not complementary with the sequence of Seq$_{sense}$ or Seq$_{antisense}$.

Said insect gene are selected from trypsin precursor gene, dopa decarboxylase gene, NADH dehydrogenase ubiquinone flavoprotein 2 gene, ATP synthase beta subunit gene, or myosin heavy chain isoform B gene.

In another preferred embodiment, said insect gene is a gene from *Helicoverpa armigera*, corn borer, aphid, or planthopper.

In another aspect of the invention, it provides uses of said constructs, wherein the uses are for producing plants with insect resistance.

In another aspect of the invention, it provides uses of interfering molecules, which can specifically interfere with the expression of insect genes, in plant insect resistance. The insect genes are selected from trypsin precursor gene, dopa decarboxylase gene, NADH dehydrogenase ubiquinone flavoprotein 2 gene, ATP synthase beta subunit gene, or myosin heavy chain isoform B gene.

In another preferred embodiment, said insect gene is a gene from cotton bollworm (*Helicoverpa armigera*), corn borer, Aphid, or planthopper.

In another aspect of the invention, it provides insect genes or fragments thereof as targets for inhibiting or silencing insect genes. The genes or fragments thereof are selected from:

A sequence at positions 1-576 of SEQ ID NO: 1 (trypsin precursor);

A sequence at positions 311-621 of SEQ ID NO: 2 (dopa decarboxylase);

A sequence at positions 291-771 of SEQ ID NO: 3 (NADH dehydrogenase ubiquinone flavoprotein);

A sequence at positions 203-630 of SEQ ID NO: 4 (ATP synthase beta);

A sequence at positions 372-662 of SEQ ID NO: 5 (Myosin heavy chain, isoform B);

A sequence at positions 501-899 of SEQ ID NO: 3 (NADH dehydrogenase ubiquinone flavoprotein 2); or A sequence at positions 251-643 of SEQ ID NO:45 (NADH dehydrogenase ubiquinone flavoprotein 2).

In another aspect of the invention, it provides a plant cell, wherein said plant cell expresses an interfering molecule that can specific interfere with the expression of an insect gene;

Said insect genes are selected from trypsin precursor gene, dopa decarboxylase gene, NADH dehydrogenase ubiquinone flavoprotein 2 gene, ATP synthase beta subunit gene, or myosin heavy chain isoform B gene.

In another preferred embodiment, said insect gene is a gene from cotton bollworm (*Helicoverpa armigera*), corn borer, Aphid, or planthopper.

In another preferred embodiment, said plant cell cannot produce a plant directly via photosynthesis in the presence of nutrients.

In view of the present description, other aspects of the invention can be readily appreciated by skilled persons in the art.

BRIEF DESCRIPTION OF THE DRAWINGS

FIG. 2A. Northern blot analysis of dsRNA abundance of NADH dehydrogenase (dsWXM-12) in transgenic *Arabidopsis* (events 12-2, 5, 6, 7, 8). WT indicates the wild type plant control.

FIG. 2B. RT-PCR analysis of dsRNA abundance of NADH dehydrogenase (dsWXM-12) in transgenic *Arabidopsis* (events 12-13, 14, 15, 16, 17, 18). WT indicates the wild type plant control.

FIG. 2C. Northern blot analysis of trypsin precursor (dsWXM-2) dsRNA expression in transgenic *Arabidopsis* (events 2-1, 2, 3, 4). WT indicates the wild type plant control.

FIG. 2D. RT-PCR analysis of dopa decarboxylase (dsWXM-6) dsRNA expression in transgenic *Arabidopsis* (events 6-2, 3, 4, 5). WT indicates the wild type plant control.

FIG. 2E. RT-PCR analysis of ATP synthase beta (dsWXM-25) dsRNA expression in transgenic *Arabidopsis* (events 25-2, 5, 9, 10). WT indicates the wild type plant control.

FIG. 2F. RT-PCR analysis of myosin heavy chain (dsWXM-E) dsRNA expression in transgenic *Arabidopsis* (E-1, 2, 7, 8, 10). WT indicates the wild type plant control.

FIG. 3A. PCR analysis of transgenic cotton (R15, 9, 10, 15, 16, 21, 22, 27, 145-1, 145-2, 145-3, 165-1, 165-2) of dswxm-12/2301. R15 indicates the recipient material of transgene.

FIG. 3B. RT-PCR analysis of dsRNA expressions in dsWXM-12 transgenic cotton (R15, 10, 16, 21, 27, 145-1, 165-1). R15 indicates the recipient material of transgene.

FIG. 3C. RT-PCR analysis of 5 randomly selected samples infected with tobacco virus (CK, 1, 2, 3, 4, 5).

FIG. 4A. Body weight increases of 3-instar *H. armigera* larvea (6 *H. armigeras* each group, in triplicates, for a total of 18 *H. armigeras*) after feeding on INT or dsWXM-12 transgenic plants (12-2) for 3 days. Worms fed on 12-2 showed less body-weight increases compared to those fed on WT or transgenic plants expressing dsRNAs of other genes (1, 5, 8, 11, 20 in the figure refer to WXM-1, 5, 8, 11, 20 genes).

FIG. 4B. Body weight increase of 3-instar *H. armigera* larvae (6 larvae each group, in triplicates, for a total of 18 worms) fed on WT or dsWXM-12 transgenic plants (12-18) for 3-7 days. The worms were weighed and body weight increases were recorded. *H. armigera* larvae fed on dsWXM-12 showed slower body-weight increase than those fed on WT or transgenic *Arabidopsis* expressing dsRNAs of other genes (27 in the figure refer to WXM-27 gene).

FIG. 4C. Body weight increase of 3-instar larvea (6 worms each group, in triplicates, for a total of 18 worms) after feeding on WT or transgenic *Arabidopsis* expressing dsWXM-2 (2-4) for 3 days. The worms were weighed and body weight increases were calculated. Body-weight increases of *H. armigera* fed on 2-4 were apparently slower than those fed on WT plants.

FIG. 4D. Body weight increases of 3-instar larvae (6 worms each group, in triplicates, for a total of 18 worms) after feeding on WT or dsWXM-6 line 2 (6-2) for 4 days. The worms were weighed and body weight increases were calculated. Body weight increases of *H. armigera* fed on 6-2 were apparently slower than those fed on WT plants.

FIG. 4E. Body weight increase of 3-instar larvae (6 worms each group, in triplicates, for a total of 18 worms) after feeding on WT, dsWXM-E line 2 (E-2) or dsWXM-25 line 2 (25-2) for 4 days. The worms were weighed and body weight increases were calculated. Body weight increases of *H. armigera* fed on E-2 or 25-2 where apparently slower than those fed on WT plants.

FIG. 5A. Transcription level of NADH dehydrogenase ubiquinone flavoprotein 2 in *H. armigera* mid gut decreased significantly after fed on transgenic *Arabidopsis* expressing dsWXM-12 (12-2) for 3 days.

FIG. 5B. Transcription levels of NADH dehydrogenase ubiquinone flavoprotein 2 in *H. armigera* mid gut decreased significantly after feeding on transgenic *Arabidopsis* expressing dsWXM-12 (12-18) for 7 days.

FIG. 5C. Transcription levels of myosin heavy chain in *H. armigera* mid gut decreased significantly after feeding on transgenic *Arabidopsis* expressing dsWXM-E (E-2) for 4 days.

FIG. 6A Mortality of 2-instar *H. armigera* larvae (6 worms each group, in triplicate, for a total of 18 worms) after feeding on R15 or transgenic cotton plants expressing dsWXM-12 for 5 days. Significantly increased mortality of *H. armigera* fed on transgenic than those fed on non-transgenic cotton plants were observed.

FIG. 6B. Mortality of 2-instar *H. armigera* larvae (6 worms each group, in triplicate, for a total of 18 worms) after feeding on WT or transgenic cotton expressing dsWXM-12 for 5 days. Significantly increased mortality of *H. armigera* fed on transgenic cotton than those fed on non-transgenic cotton plants were observed.

FIG. 6C. Body weight increases of 3-instar *H. armigera* larvae (6 worms each group, in triplicate, for a total of 18 worms) after feeding on VIGS tobacco plants expressing dsWXM-12 for 5 days. The body weight increases of insects were recorded. Those fed on dsWXM-12 plants showed significantly slower body weight increase than those fed on WT plants.

FIG. 6D. Body weight increased of 3-instar *H. armigera* larvae (6 worms each group, in triplicate, for a total of 18 worms) after feeding on VIGS tobacco plants expressing dsWXM-12(501) for 5 days. The body weight increases of insects were recorded. Those fed on dsWXM-12(501) plants showed significantly slower body weight increase than those fed on WT plants.

FIG. 6E. Mortality of 2-instar larvae of *O. furnacalis* (corn borer) (6 *O. furnacalis* each group, in triplicate, for a total of 18 *O. furnacalis*) after feeding on WT or VIGS tobacco plants expressing dsWXM-corn (homologous gene of NADH dehydrogenase ubiquinone flavoprotein 2 in *O. furnacalis*) for 3 days. Those fed on VIGS tobacco plants expressing dsWXM-corn showed significantly increase of mortality than those fed on WT or VIGS plants containing empty vector.

FIG. 7A Transcription level of NADH dehydrogenase ubiquinone flavoprotein 2 was significantly lower in those fed on dsWXM-12 VIGS tobacco plants than in those fed on WT plants.

FIG. 7B Transcription level of NADH dehydrogenase ubiquinone flavoprotein 2 was significantly lower in those fed on dsWXM-12(501) VIGS tobacco plants than in those fed on WT plants.

Figure 1A:
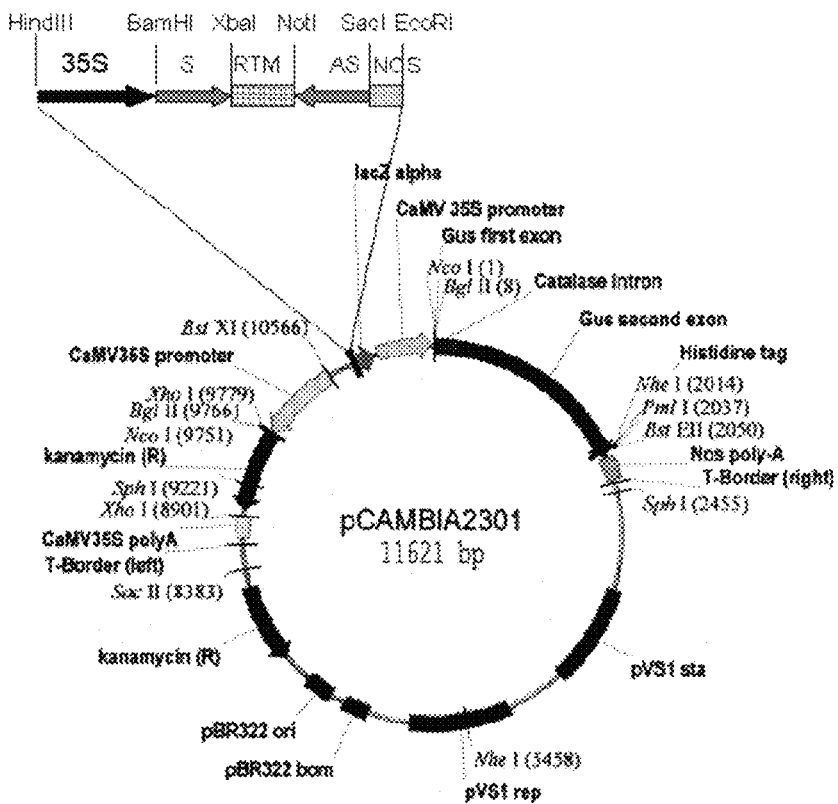
FIGS. 1A and 1B show schematic of dsRNA vectors and VIGS vectors.

DETAILED DESCRIPTION OF THE
PREFERRED EMBODIMENT

After extensive and thorough research, the inventors found some target genes from insects. Based on nucleotide sequences of these target genes, constructs may be designed to form interfering RNA in plants to interfere with these target genes. After said plants are eaten by insects, expression of the corresponding genes can be significantly inhibited. This inhibition is hardly or not at all affected by the barriers of the insect digestive systems. Thus, the transgenic plants expressing interfering RNA of insect genes, after being eaten by plant-eating insects and entering insect bodies may be used to interfere with or inhibit the expression of target genes in plant-eating insects to achieve insect controls.

Definitions

As used herein, the term "plant" is not particularly limited, as long as the "plant" is easily infested by insects (e.g., Lepidoptera), such as various crops, flower plants, or forestry plants. The plant may be (but is not limited to): dicotyledon, monocotyledon or gymnosperms. More specifically, the plants may include (but are not limited to): cotton, wheat, barley, rye, rice, corn, sorghum, sugar beet, apple, pear, plum, peach, apricot, cherry, strawberry, raspberry, blackberry, beans, lentils, peas, soybeans, rapeseed, mustard, poppy, oleanolic, sunflowers, coconut, castor oil plants, cocoa beans, peanuts, gourd, cucumber, watermelon, flax, hemp, jute, oranges, lemons, grapes grapefruit, spinach, velvetleaf lettuce, asparagus, cabbage, Chinese cabbage, Chinese cabbage, carrots, onions, potatoes, tomatoes, green peppers, avocados, cinnamon, camphor, tobacco, nuts, coffee, eggplant, sugar cane, tea, pepper, vines Oyster Asakusa, bananas, natural rubber trees and ornamental plants, etc.

As used herein, the term "insect" refers to any insect containing in its genome a gene selected from the group consisting of trypsin gene, dopa decarboxylase gene, NADH dehydrogenase flavoprotein 2 gene, ATP synthase beta subunit gene, myosin heavy chain subtype B gene, and these genes are necessary for growth or survival of the insect. Preferably, the insects can be a plant-eating phytophagous insects, such as Collembola, Isoptera, Coleoptera, Diptera, Hymenoptera, Lepidoptera, Orthoptera, Hemiptera, Thysanoptera insects or agricultural pests. Specific example includes long-winged tortrix moth species, genus of adoxophyes, clearwing, cutworm, Cotton leaf corrugated armyworm, *Anticarsia gemmatalis*, archips, argyrotaenia, *Noctua*, Busseolafusca, Pink spotted frog, *Carposina sasakii*, frog, *choristoneura, clysia ambiguella*, leaf rollers frog, cnephasia, Coleophora, *Thaumatotibia leucotreta*, leaf roller, Corn frog, Leaf pine needles Moth, diamond, pink frog, *eucosma, Euproctis flava* Bremer, cutworm, *leguminivora, hedya, Noctua*, Choi frog, *Hyphantria cunea, Keiferia lycopersicella Walsingham, Leucoptera scitella, conopobathr, Lymantria, phyllocnist, Malacosoma, Mamestra brassicae, Manduca sexta, Apochemia*, European corn frog, *pammene, panolis*, Pink bollworm, cotton bollworm, *Pieris rapae Phthorimaea operculella, Pieris*, diamondback moth, ermine moth, white wild frog, big frog, *Zeiraphera Acanthocolla, paranthrene, argyrotaenia, tortrix*, cabbage looper, tree ermine moth, Elateroidea, snout beetle, atomaria linearis, beet stem flea beetle, *sitophilus*, real image genus, *dermestes, LeptispaBaly, Coccinella, Leptinotarsa decemlineata, Echinocnemus squameus Billberg, Melolontha, tenebroides, Cleoninae, Anomala exoleta Faldermann altica, Bostrichus*, scarab: *Sitophilus oryzae, sitotroga, Tenebrionini, Tribolium, Trogoderma*, genus beetles, flour beetlegenus, Genus *Gryllotalpa*, the case of the beetle, flea beetle genus, genus non-*Blatta Blatta, Leucophaea maderae*, Locusts, *Periplaneta*, grasshoppers, termites, *thrips, Thrips*, single *thrips, Thrips palmi, Thrips, Scirtothrips aurantii* Faure. More preferably, said insects are harmful to plants. Chinese patent application No. 200680042821.5 and US 2009/0306189 A1, WO 2007/080127 A2, AU 2006/335978 A1, US 2009/0285784 A1 are references for this invention, description of insects on page 41-47 in CN101365795 is incorporated into the specification of this invention.

Herein the term "RNA interference" (RNAi) refers to blocking, using certain double-stranded RNAs, the expression of specific genes in vivo with high efficiency and specificity, facilitating mRNA degradation, and inducing cells to exhibit specific gene deletion phenotype. This process is also referred to as RNA intervention or interference. RNA interference is highly specific gene silencing mechanism on the mRNA level.

In the present invention, the basic principles of RNA interference are as follow: using plants as intermediate, allowing insects to ingest interfering RNAs capable of interfering with insect genes (including: trypsin precursor gene, dopa decarboxylase gene, NADH dehydrogenase ubiquinone flavoprotein 2 gene, ATP synthase β subunit gene, myosin protein heavy chain isoform B gene), leading to inhibition of insect growth or to killing insect. In particular, the principles are as follow: using gene transfection methods to express double-stranded RNAs (dsRNAs) of insect genes (full- or partial-length) in plant to produce high levels of interfering RNAs in plants. When insects ingest such transgenic plants, large amounts of interfering RNAs are ingested simultaneously. After entering inside insect bodies, the interfering RNAs may in turn inhibit the expression of insect genes resulting in the inhibition of normal insect growths/developments, or even death. Based on the described principles, the ability of plants to resist insect can be effectively improved. Applying RNA interference techniques to transgenic plants to develop new type of transgenic resistant plants has great significance to the development of agriculture.

Herein, the term "interfering molecules" generally refers to a kind of substance having insect prevention activity obtained from preparing or processing (such as in vivo processing) insect genes or their fragments (truncated form) as targets based on the present invention. Said "interfering molecules" include, for example, dsRNA, antisense nucleic acid (nucleotide), small interfering RNA, miRNA, etc.

As used herein, the term "dsRNA" refers to a double-stranded RNA molecule, which can degrade specific mRNA by targeting mRNA with homologous complementary sequences. This process is referred to as RNA interference pathway.

As used herein, "basically complementary" refers to nucleotide sequences being sufficiently complementary, which can interact with each other in a predictable manner, such as forming secondary structure (such as stem-loop structure). Usually, there is at least 70% of nucleotides are complementary between two "basically complementary" nucleotide sequences; preferably, at least 80% of nucleotides are complementary; more preferably, at least 90% of nucleotides are complementary; even more preferably, at least 95% of nucleotides are complementary; for example, 98%, 99% or 100%. Usually, there is at most 7 mismatched nucleotides between two sufficiently complementary molecules; preferably, there is at most 6 mismatched nucleotides; more preferably, there is at most 5 mismatched nucleotides; even more preferably, there is at most 4 mismatched nucleotides; for example, there is 0, 1, 2, 3, and 4 mismatched nucleotides.

As used herein, "complementary" sequences usually refer to converting the sequence with direction of 5'-3' to 3'-5' (such as 5' ATCG 3' →GCTA), then obtain its complementary sequence (such as GCTA→5' CGAT 3').

As used herein, "stem-loop" structure also called "hairpin" structure, which refers to a kind of nucleotide molecules capable of forming a secondary structure having double-stranded region (stem part), said double-stranded region is formed by two regions (located at the same molecule) of the nucleotide molecule, two regions flank the double-stranded region; it also includes at least one "loop" structure containing non-complementary nucleotide molecule, which is single-stranded region. Even if two regions of the nucleotide molecule are not completely complementary, the double-stranded region of the nucleotide can still maintain the double-stranded condition. For example, insertion, deletion, replacement, etc., may lead to a small non-complementary region or the small region self-forming a stem-loop structure or other forms of secondary structures. However, these two regions are still basically complementary, and can interact with each other in a predictable manner, forming double-stranded regions of a stem-loop structure. Stem-loop structure is well known by skilled persons in the art. Usually, after obtaining a nucleic acid having a nucleotide sequence with primary structure, skilled persons in the art can determine whether the nucleic acid is capable of forming a stem-loop structure or not.

As used herein, said "operably linked" or "operatively linked" refers to spatial arrangement of functionality of two or more nucleic acid regions or nucleic acid sequences. For example: promoter region is placed at a specific position relative to the nucleic acid sequence of target gene, causing the transcription of nucleic acid sequences guided by the promoter region. Thus, promoter region is "operably linked" to the nucleic acid sequences.

As used herein, unless otherwise stated, in the term "insect resistance", said "insect" represents "pest".

As used herein, said "contain", "have" or "including" include "comprising", "mainly consist of", "basically consist of" and "formed of"; "primarily consist of", "generally consist of" and "comprising of" belong to generic concept of "have" "include" or "contain".

Methods of determining sequence identity are conventional for skilled persons in the art, including using Blast software and EMBOSS software (The European Molecular Biology Open Software Suite (2000), Rice, P. Longden, I. and Bleasby, A. Trends in Genetics 16, (6) pp 276-277). As used herein, the term "identity" refers to the relationship between sequences at the nucleic acid level. Through comparing the sequences (such as, two or more) with optimal alignment in the comparison window, "identity percentage" can be determined. Herein, the comparison between said sequences in the comparison window and the reference sequence with optimal sequence alignment may contain insertion or deletion. Said reference sequences do not contain insertion or deletion. Said reference window is selected from at least 10 consecutive nucleotides up to about 50, about 100, or up to about 150 nucleotides, preferably about 50-150 nucleotides. Then, by detecting the number of identical nucleotides between sequences in said window and divided the above number by the number of nucleotides in said window and multiplied by 100 to calculate "identity percentage".

Gene

Basic unit of genetic message of encoded proteins or RNA, etc., having specific functional products and is a fragment of DNA sequence of chromosome or genome (as to RNA viruses that use RNA as carrier of genetic message, it's RNA sequence). It includes coding sequences (exons), sequences having regulatory function on gene expression located before and after coding region and intervening sequences (introns) located between individual coding sequences.

Target Gene

Methods of the present invention use plants as intermediate, through allowing insect ingest interfering RNA capable of interfering insect gene expression, to inhibit insect growth or to kill insects. To find out insect genes suitable for this operation, after extensive and thorough research, the inventors finally found suitable genes. Said genes include trypsin precursor gene, dopa decarboxylase gene, NADH dehydrogenase ubiquinone flavoprotein 2 gene, ATP synthase β subunit gene, and myosin heavy chain isoform B gene. The main activities or functions of these gene-encoded proteins are as follow:

Trypsin precursor is a digestive enzyme, mainly exists in the midguts of some insects, and is used to digest in-take proteins, make them into smaller polypeptides or amino acids for further absorbance and metabolism.

Dopa decarboxylase is a kind of amino acid decarboxy-lase, catalyzes dopa decarboxylation to produce dopamine.

It is a key enzyme in the process of biosynthesis of tanning agent, N-acetyl dopamine in insects, relating to stratum corneum tanning during insect pupa formation period.

NADH dehydrogenase ubiquinone flavoprotein 2 is a subunit of energy metabolism Complex I in mitochondria, catalyzes NADH oxidation to $NAD^+$ and $H^+$, and release electrons for subsequent energy transfer reactions.

ATP synthase beta is widely present in mitochondria of animals. It is a key enzyme in energy metabolism in organisms, participating in oxidative phosphorylation reaction, catalytically synthesizing ATP driven by motive force of membrane-crossing protons. ATP synthase is a complicated complex, composed of multiple subunits, including subunit.

Myosin (Myosin heavy chain, isoform B) is a constituent unit of heavy myofilament. It is present in the smooth muscle, and plays an important role in muscle movement. Myosin is composed of two identical heavy chains and two pairs of light chains. Heads of heavy chains have ATP enzyme activity and bind actin.

Down-regulation or inhibition of expression of these genes may lead to problems of insect growth or death. Said genes can be used as targets for inhibition or silencing to produce specific interfering molecules, inhibiting growth or development of *Helicoverpa armigera* or killing them. The present invention also obtain highly homologous genes to said genes from *Ostrinia furnacalis*, using them as targets for inhibition or silencing, to produce specific interfering molecules, inhibiting growth or development of *Ostrinia furnacalis* or killing them. Said genes can be also obtained from other organisms, functions of said genes have been established in literature, their nucleotide sequences are highly homologous to that in *Helicoverpa armigera*. It is conceivable that these highly homologous genes can be used as targets, to produce specific interfering molecules, to inhibit growth or development of organism from which said genes were isolated or to kill them.

These genes or their encoded proteins are conservatively and widely present in insects, including major pests: Aphid, corn borer, planthopper, etc. These genes or their encoded proteins exhibit similar functions in said pests, please see Table 1 for homology comparison of partial gene sequences. It is conceivable that trypsin precursorgene, dopa decarboxylase gene, NADH dehydrogenase ubiquinone flavoprotein 2 gene, ATP synthase β subunit gene, myosin heavy chain isoform B gene from Aphid, corn borer, planthopper, etc., respectively, can be target genes for designing interfering RNA to resist Aphid, *Ostrinia nubilalis*, planthopper, etc.

Due to similar functions of each of the above-mentioned gene encoded proteins in different insects, therefore, polynucleotides with nucleotide sequence homology no less than 50% in trypsin precursor gene, dopa decarboxylase gene, NADH dehydrogenase ubiquinone flavoprotein 2 gene, ATP synthase β subunit gene or myosin heavy chain isoform B gene present in other insects and *Helicoverpa armigera* are also included in the present invention, serving as targets for designing interfering RNAs. Preferably, polynucleotides with nucleotide sequence homology no less than 55%, 60%, 65%, or 68% in trypsin precursor gene, dopa decarboxylase gene, NADH dehydrogenase ubiquinone flavoprotein 2 gene, ATP synthase β subunit gene or myosin heavy chain isoform B gene present in other insects and *Helicoverpa armigera* are also included in the present invention, serving as targets for designing interfering RNA. More preferably, polynucleotides with nucleotide sequence homology no less than 70%, 71%, 75%, 79%, or 80% in trypsin precursor gene, dopa decarboxylase gene, NADH dehydrogenase ubiquinone flavoprotein 2 gene, ATP synthase β subunit gene or myosin heavy chain isoform B gene present in other insects and *Helicoverpa armigera* are also included in the present invention, serving as targets for designing interfering RNA. Even more preferably polynucleotides with nucleotide sequence homology no less than 83%, 85%, 90%, 92%, 95%, 96%, 97%, 98%, or 99% in trypsin precursor gene, dopa decarboxylase gene, NADH dehydrogenase ubiquinone flavoprotein 2 gene, ATP synthase β subunit gene or myosin heavy chain isoform B gene present in other insects and *Helicoverpa armigera* are also included in the present invention, serving as targets for designing interfering RNAs.

Based on extensive and thorough research, the inventors found these proteins encoded by the target genes or their fragments play important roles in insects. When they are inhibited, interfered or silenced, it will lead to significant inhibition of insect growth or a significant decrease in survival rates. Thus, one can design various interfering molecules based on these target genes or their homologous genes and their fragments, which can be used for pest control.

Constructs can be designed based on the sequences of above target genes or gene fragments, or their homologous genes to express double-stranded RNAs (dsRNAs) that specifically interfere insect gene expressions in plants.

TABLE 1

| Gene Name | *Helicoverpa armigera* | | Aphid | | *Ostrinia nubilalis* | | Planthopper | |
|---|---|---|---|---|---|---|---|---|
| | GenBank Number | Homology (Sequence Identity) | GenBank Number | Homology* (Sequence Identity) | GenBank Number | Homology* (Sequence Identity) | GenBank Number | Homology (Sequence Identity)* |
| trypsin precursor gene | EE399600.1 | 100% | | | AY953059 | 71% | | |
| dopa decarboxylase gene | EE399464.1 | 100% | XM_001950520 | 65% | | | | |
| NADH dehydrogenase ubiquinone flavoprotein 2 gene | EE399580.1 | 100% | XM_001946866 | 68% | GH999345 | 79% | DB857837 | 68% |
| ATP synthase gene | EE399658.1 | 100% | NW_001919738 | 77% | GH995948 | 84% | DB829492 | 83% |
| Myosin gene | EE3 99482.1 | 100% | XM_001952178 | 75% | HQ116666 | 71% | DB853308 | 78% |

*represent the homology of gene in this insect as compared to the protein/gene in *Helicoverpa armigera*.

Length of said gene fragments is at least 18 bp, preferably at least 20 bp, more preferably at least 50 bp, even more preferably at least 100 bp, more preferably 100-700 bp; more preferably 200-600 bp.

For example, said gene fragment is selected from: 1-576 bp of SEQ ID NO: 1 (trypsin precursor); 311-621 bp of SEQ ID NO: 2 (dopa decarboxylase); 297-771 bp of SEQ ID NO: 3 (NADH dehydrogenase ubiquinone flavoprotein 2); 203-630 bp of SEQ ID NO: 4 (ATP synthase beta); or 372-662 bp of SEQ ID NO: 5 (Myosin heavy chain, isoform B).

The present invention also provides a polynucleotide set, said polynucleotide set contains the following sequences: SEQ ID NO: 1 or its 1-576 bp; SEQ ID NO: 2 or its 311-621 bp; SEQ ID NO: 3 or its 297-771 bp; SEQ ID NO: 4 or its 203-630 bp; or SEQ ID NO: 5 or its 372-662 bp. One or more polynucleotides can be used to prepare insect resistant transgenic plants or preparing pest control interfering molecules. They may achieve a broader and a more effective insect killing effect if they were used together.

Constructs

According to gene sequences provided by the present invention, polynucleotide constructs of interfering molecules (such as dsRNA) capable of affecting corresponding mRNA expression in insects can be designed and transformed into plants for processions. Thus, the present invention provides an artificially made construct. Based on gene sequences provided by the present invention, designing said constructs is known by skilled persons in the art. Usually, said construct may contain an intron sequence (non-complementary to two flanking sequences) and complementary gene sequences that are linked at two ends of the intron. After transfecting into cells, it can form a "stem-loop" structure, in which the "stem" region can be processed by plant cells to form interfering molecules (such as dsRNA). This kind of interfering molecules can be specifically effective in inhibiting target gene expression.

In accordance with one preferred embodiment of the present invention, said construct contains at least one of the following structures:

$$\text{Seq}_{sense}\text{-X-Seq}_{antisense};\quad\text{Formula I}$$

Wherein, $\text{Seq}_{sense}$ and $\text{Seq}_{antisense}$ are basically complementary nucleotide sequences, after transfected into plants, $\text{Seq}_{sense}$ and $\text{Seq}_{antisense}$ can form interfering molecules capable of specifically interfering with insect gene expression;

X is an intervening sequence located between $\text{Seq}_{sense}$ and $\text{Seq}_{antisense}$, and said intervening sequence is not complementary with $\text{Seq}_{sense}$ and $\text{Seq}_{antisense}$.

Structure shown in Formula I after being transfected into plant cells, it forms a secondary structure as follows:

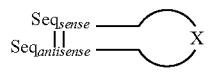

Formula II

In plants, the structure is further cleaved, and processed to be interfering molecules (such as dsRNA), exhibiting gene silencing effect.

Said constructs can be prepared to form of more than one "stem-loop" structure, such as, containing two or more than two "stem-loop" structures, the "stem" regions of these stem-loop structures (formed as a result of interaction between $\text{Seq}_{sense}$ and $\text{Seq}_{antisense}$).

Methods of Improving Insect Resistance in Plants

The present invention also provides methods of improving insect resistance in plants, including expressing interfering molecules (such as double-stranded RNA (dsRNA)) that specifically interferes insect gene expression in plants; said insect gene is selected from trypsin precursor gene, dopa decarboxylase gene, NADH dehydrogenase ubiquinone flavoprotein 2, ATP synthase β subunit gene, myosin heavy chain isoform B gene. Thus, after insects ingest the plants (transgenic plants), said insect gene expression is down-regulated in vivo and their growths are inhibited.

As preferred embodiments of the present invention, said embodiments include steps: (a) providing said construct; (b) transfecting said construct in (a) into plants, thereby, expressing said interfering molecules (such as dsRNA) included therein, said interfering molecules can inhibit the expression of corresponding genes in insect that ingest the transgenic plants, thus improving insect resistant ability in plants.

Transforming plants with recombinant DNA can be carried out via conventional techniques well known to skilled persons in the art and specific methods depends on the species of plants used. For example, one may use *Agrobacterium tumefaciens* transformation or gene gun transformation methods, etc., such as leaf-disc method, rice embryos transformation method, etc. For the transformed plant cells, tissues or organs, conventional methods can be used to regenerate new plants.

Usually, said constructs are located on expression vectors. Thus, the present invention also includes a kind of vectors, which contain said constructs. Said expression vectors usually further contain promoter operably linked to said constructs, replication origins and/or marker genes, etc. Expression vectors required in the present invention can be constructed using methods well known to skilled persons in the art. These methods include in vitro recombination DNA techniques, DNA synthesis techniques, in vivo recombination techniques, etc. Said expression vectors preferably include one or more selection marker genes, to provide phenotypic characteristics for selecting transformed host cells, such as resistance to kanamycin, gentamicin, hygromycin and ampicillin.

Vectors harboring the above-mentioned suitable gene sequences and suitable promoters or controlling sequences may be used to transform suitable hosts. In methods of the present invention, said hosts may be any hosts carrying said expression vectors and also can transfer said expression vectors into plant cells in hosts. Preferably, said host is *Agrobacterium tumefaciens*.

As a preferred embodiment, said methods of transferring constructs into plants including:

(1) providing *Agrobacterium tumefaciens* carrying expression vector, said expression vector contains said construct;

(2) contacting plant cells, tissues or organs with *Agrobacterium tumefaciens* in step (1), thereby, transfecting said construct into plant cells, tissues or organs;

(3) selecting the plant cells, tissues or organs transfected with said constructs.

(4) regenerating the plant cells, tissues or organs in step (3) into plants.

The present invention also provides a kind of plants, in which interfering molecules that specifically interfere with the expression of insect genes are expressed; or said polynucleotide constructs are included therein. Said plants are prepared and obtained by using said transgenic methods.

Advantages of the Present Invention Include (1) Technical resolutions of the present invention use plants as intermediates, to inhibit insect growth or survival via RNA interfering mechanism, and provide suitable insect target genes for RNA interfering. After transferring into plants the constructs designed according to those gene sequences, the formed interfering molecules ingested by insects are little or not affected by barriers, such as digestive system, in insects.

(2) Methods of the present invention can improve insect resistance in plants, reduce pesticide application, lower agricultural production cost of and protect ecological environment.

The present invention may be further illustrated by a combination of the following specific embodiments. It should be understood that these embodiments are only used for illustrating the present invention and not for limiting the scope of the present invention. Detailed experimental conditions not provided in the following embodiments are generally performed according to conventional conditions, such as those described in Sambrook and Russell (2001). Molecular Cloning: A Laboratory Manual (3rd ed.); Cold Spring Harbor Laboratory Press or according to conditions suggested by the manufacturers. Unless otherwise stated, the percentage and fraction will be calculated by weight.

Unless otherwise defined, all the technical and scientific items have the same meaning well known to skilled persons in the art. In addition, any methods and materials similar with or identical to the recorded content can also be used in the present invention. Preferred embodiments and materials described herein are used only as demonstrations.

Example 1, Sequences of Fragments Used for Constructing dsRNA Vectors

Using *H. armigera* cDNA library (ZAP express) (cDNA library was constructed using total RNA extracted from the midgut of 5-instar *H. armigera* larvae fed with artificial diet containing 1 mg g$^{-1}$ gossypol for one day) as template, 29 gene fragments were amplified and used for constructing dsRNA expression vectors, which are referred to as WXM-1~WXM-29. Genes related to EST fragments herein are shown in Table 2.

TABLE 2

| WXM-1 | Chymotrypsin precursor |
|---|---|
| WXM-2 | Trypsin precursor |
| WXM-5 | Juvenile hormone diol kinase |
| WXM-6 | Dopa decarboxylase |
| WXM-8 | ATP synthase beta subunit |
| WXM-11 | NADH-ubiquinone oxidoreductase |
| WXM-12 | NADH dehydrogenase ubiquinone flavoprotein 2 |
| WXM-20 | Mitochondrial ATP synthase alpha subunit precursor |
| WXM-25 | ATP synthase beta |
| WXM-27 | Lipase-1 |
| WXM-E | Myosin heavy chain, isoform B |

In the present invention, coding sequences of trypsin precursor gene, dopa decarboxylase gene, NADH dehydrogenase ubiquinone flavoprotein 2, ATP synthase β subunit gene, myosin heavy chain isoform B gene and RTM intron sequences are used. In them, underlined regions indicate fragments used for constructing dsRNA vectors.

```
SEQ ID NO: 1 (WXM-2, coding sequence of trypsin precursor, GenBank:
EE399600.1):
ACCCTACTATTGCGGCTCTTCTCTACACCTGGAACTGGAGCACCTACTGGCAGGCTTGCGGCGGTAC

CATCATCAACAACCGCTCCATTCTTACCGCCGCTCACTGCACCCAAGGTGACGCCCCTGGCAGATGGC

GTATCCGTGTTGGCTCCACCTGGGCCAACAGCGGTGGCGTTGTCCAACGTTAACCTGAACATCGT

CCACCCCTCATACAACTCCAACACTCTGAACAATGACATCGCTCTCCTGCGCTCCGCCACCACCTTCT

CCTTCAACAACAACGTGCAAGCCGCTCCCATTGCAGGCTCCAACTACAACCTTGCTGCCAACCAGTTT

GTCTGGGCTGCTGGATGGGGCACTATCTCCTCCGGTGGTGCTGCCTCCGAGCAACTCCGTCACGTGC

AGCTGATTGTCATCAACCAGAACACTTGTGCTAGCAACTACGCTTCTGCTGGTGTCACCATCACCAAC

AACATGTTGTGCTCCGGCTGGAACGGCGGTGGTCGTGACCAGTGCCAGGGAGACTCCGGCGGTCCT

CTCTACCACAACGGCATCGTTGTCGGTGTCTGCTCCTTCGGTATTGGATGCGGTCTCGCTAACTTCC

CTGGTGTGAACGCTCGCGTATCTCAGTACACCTCTTGGATCAACAGCAACGCTTAAGAAGTGTAATG

AGGAAATATATTGTTGATGATTTTATGATATGCCTAAAAAAAAAAAAAAAAA

SEQ ID NO: 2 (WXM-6, coding sequence of dopa decarboxylase, GenBank:
EE399464.1):
AGGCCCCTTGGGCAAAAGTGGAACGTGTTCCAGCATGAACTTGTTGCGTGAGCCCAGCTTACGGATC

CGCCTCATTGGCTGAATCGTAACTCATGAAGCGTGAAAGCGGATCTTCGATTCGATCCACACAAGTG

ATGCTCGTACTCGACTGTTCCGCCATGTGAGCTCAAAGAACGCGGTGGATCGTCGATGCTCAATGTC

GATCCCTGTACTGAACACGACAGCAGGGATCAGCTCCAGACTACCGTCACTGGCAAATACCACTTGG

ACGTCGTTTCAGAGCGCTTAAGTTGTGGTTCGTTTTACGTCTGTATGGCGTGGAGAATCTCCAGAAG

CACATCAGAAAACACATTGCGCTTGCCCATCTATTTGAAAAATTGTGCAGCGCTGACGAAAGGTTCGA

AATTTATGAAGAAGTGACTATGGGACTTGTCTGCTTTAGACTAAAGGCGGTAACGAAAAGAATGAG
```

-continued

GAACTGCTCAGGCATATAAATGGAAGAGGCAAAATTCATTTAGTTCCTTCTAAGATCGACGACACATA

CTTCCTTCGATTAGCAATTTGCTCACGTTTCACCGAAGATAGTGACATTCATATATCTTGGGAGGAAG

TAAAGGCTGCTGCTGATGATGTACTTAAAGGTCACTGAATCGCTTTGCATTTCAATATAATAGCAATA

ATTAGAGCCAAAACATAAATTAGACAACAATGCTGCTACTTTCTTTAAAGCAGGAGAGAAACGAGATA

TTTAAAGATTATTAAAATTTGATGGTATTTATTGTATTTAGATGCACAGTATATGTAACTATGGTAAC

TGTGATAGAAAAATGTTTAGTAAAAGAATTGTAGTGCCGTTTGTGACAATAAATATCTAAATAAGATG

TCTTCTCCCGTAATTATTTATTATTACTGACAATAATAAAATGATTGTTCTTTCCTATTTTAGAACAAT

ATTTTTGTGTTCAATGTTATTTAATAATCAGTTTTAATGTCACTAGATTAATTAATTTTGGTTCATTAA

TTGTGTAATTATATTCATATTATAATAATTTAGCTAATTAAATGCCGTTCGTTGCCTATAAAAAACAA

AAAAAAAAAAA

SEQ ID NO: 3 (WXM-12, coding sequence of NADH dehydrogenase
ubiquinone flavoprotein 2, 24 kDa, GenBank: EE399580.1):
CGCTAGCTGATACGCAGCTGATTACTTACTAGGAACAAAGCTGAGCTCGCCGCCCTGCAGTCGAATA

GGGATCAAGAATCGCCACGAGGGTTGCGACAGTGTTCGCATATTATTTCAATAAATCTAAACACAGA

TTTGTACATTACATGCTTTCAGCTGAGGACTGGAGTTCAGGGCGTGTGGCGTGCTGCATCCAGGAGT

ATTCAGACCAGCTCAGCTCTTCAACATGACAGTCTGTTCGTTCATCGTGATACTCCTGAGGACAACCG

TGATATCCCGTTCGAGTTTTCAGAGGCCAACAAGAAGAGAGTGGAAGCCTTACTAGGAATCCATCCT

GAAGGCCACAAGCGTGGTGCCATGATCCCACTGCTCGACCTGGCTCAGCGTCAGGCTGGAGGTTGG

CTGCCGATATCTGCCATGCATAAAGTAGCTGAAATCCTCAAACTTCCTCGCATGAGAGTTTATGAGGT

TGCTACGTTCTACACTATGTTTATTAGACGACCAATCGGCAAGTACCATATCCAAGTTTGCACGACAA

CTCCTTGCTGGCTCCGAGGTTCTGATGCTATCCTGAAAGCTCTCACTGAGGGTACACAATGCCATGT

TGGAGGAAACAGCCCTTGTGGCAAGTTCTCTATTTCTGAGGTTGAATGCCTTGGTGCCTGTGTTAAT

GCTCCTATGATTCAAGTCAACGATGATTACTACGAAGACCTGTCAGTAGATGACACAAAGGAAATTAT

TGAAAAGCTCAAAAGGGACGAGAAACCGAAAGCTGGCCCTAGGAGCGGCAGATTCGCCTCAGAACCC

TTGGGAGGACTCACTTCTCTCACCGAAGAACCTACAGGCCCCGGTTTTGGACTACAACCCGGCCTCA

AGGCCTAGAACAAAAGTTTCCGTTTTGTAAATTTTATTTATAGGCAATATTTAAATAAATCATGTTA

GAATCGTAAAAAAAAAAAAAAAAAA

SEQ ID NO: 4 (WXM-25, coding sequence of ATP synthase beta, GenBank:
EE399658.1):
ATAAAGTCTCACGGAGGTAGCAACAGGAAGAAATAAATGGTGGGTGCAAATAGTAGGCGATGCGTG

GCCTGTGTCTGTTGTTTATGCGAATTCAGCAACAATCAAGGCCCTGGGAAAACTTAAAGAACCCTGC

CCCCTGCCACCACCTCGCCCATTAGACCCCACCCCTTGTACTTTCCCGTGCCATTGCTGAGCTAGATA

TCTACCTTGCTGTGAACCCTCTGACTCCCACATCTGTATCATGACCCAACATATGAGCTGAGCACTAC

AACGTTGCCCGTGGTGTCCAGAAGATCTGCAGGACTACAAGTCACTCCAGGACATTATTGCTATCCT

GGGTATGGATGAGTTGTCTGAAGAAGATAAGCTGACTGTGGCTCGTGCCCGTAAGATCCAGAGGTTC

TTGTCTCAGCCTTTCCAGGTGGCTGAGGTGTTCACTGGACATGCTGGCAAACTGGTCCCCCTTGAGG

AAACTATCAAGGGCTTCTCTAAAATCCTGCAGGGCGAGTATGATCATCTACCTGAAGTAGCGTTCTAC

ATGGTTGGACCCATTGAGGAAGTTGTGGCTAAGGCCGAAACCCTGGCTAAGTCGTAAATCACAGGGA

GAGAGATGTTGAGGCAGGCACCATTATAAATCCGTAATAAGTTGTTGGCACATGTATGCATGAGGGA

GTTATGTTATTTCTAAATAAACTTAGTGGAAAATATCTATAAGAAAAAAAAAAAATATAAAAAAAAAA

AA

-continued

SEQ ID NO: 5 (WXM-E, coding sequence of Myosin heavy chain, isoform B, GenBank: EE399482.1):
CGAAAGCTGCGAGACCTGGCATCCGTAGCCTTGGGCGAGCTTCAAAGAGCTTAGAGACTCCGAGGG

GGAAGGCCAGAAGGGCAATGGTGACCCGCCGTCTGCGGACGAGCTGGCGGCGAACCAGGTCAAGCC

CAGACCAGGAGAAACTCCGCAGGCCTTGAACAAACAGATTCAGGAACTGCAGGTCAGGCTGGATGAG

GCCTGAAGGCCAAACGCCTTAAGGGAGGCAGGAAGGGCCATCCAGAAACTGGAACAGAGGGTCAGG

GAGCTCGAGAACGAGCTTGACGGTGAACAGAGGAGACACGCTGACGCCCAGAAGAACCTCCGCAAGT

CCGAGAGGCGCATCAAGGAGCTCACCTTTCCAGGCCGAGGAGGACCGCAAGAACCACGAGCGCATGC

AGGACCTCGTCGACAAACTGCAACAGAAGATCAAGACCTACAAGAGGCAGATCGAGGAAGCCGAAGA

AATCGCCGCCCTCAACTTGGCTAAGTTCCGCAAGGCACAGCAGGAGTTGGAGGAGGCCGAGGAAAG

GGCAGACCTTGCCGAGCAGGCCATCAGCAAATTCCGTGGCAAGGGACGTGCGGGTTCCGCTGCGAG

AGGAGTCAGTCCGGCGCCCCAGCGCTCGCGTCCCGCCTTCGCTGACGGTTTCGGCACCTTCCCACCA

AGGTTCGACCTGGCGCCCGAAGATTTCTAAACGTTCCACTACAGAAAAAAAACGGACTGTACAGATTT

TTCGTTGAAATGTAACTAATTTTTTTTATACATAGCAGTTGAAAGTTACGAATGCGTGAAACGAAAA

ACTGTAAAAAAAAATTTTGTAAGCCAACAAAAAAAATATACACTTTAGTGATCTAATCTTTTTACGAAA

GGCTATTTTGTAACTTGTTGATATTTATTTATATTATTTATTACCGTGGAGTATGTATCGAGAGTGCG

AGGCCGCGAGAGACGCGCGTGAGCCGCGCGCGCATGTTCGACCGAGACACGCCCCCCACCTCCG

TACCGCCGCCGGCGCGCGCGCCTCTCTCGAACGCCTCATTTTGACATCTAATAAAGCGATATGGTTG

TCATAAAATACTAAAAAAAAAAAAAAAAAAA

SEQ ID NO: 6 (RTM intron):
ACGTTGTAAGTCTATTTTTGACTCTTCTTTTTCTCCGTCACAATTTCTACTTCCAACTAAAATGCTAA

GAACATGGTTATAACTTTTTTTTATAACTTAATATGTGATTTGGACCCAGCAGATAGA

SEQ ID NO: 3 (the second fragment region, WXM-12(501), coding sequence of NADH dehydrogenase ubiquinone flavoprotein 2, 24 kDa, GenBank: EE399580.1 NADH dehydrogenase)
CGCTAGCTGATACGCAGCTGATTACTTACTAGGAACAAAGCTGAGCTCGCCGCCCTGCAGTCGAATA

GGGATCAAGAATCGCCACGAGGGTTGCGACAGTGTTCGCATATTATTTCAATAAATCTAAACACAGA

TTTGTACATTACATGCTTTCAGCTGAGGACTGGAGTTCAGGGCGTGTGGCGTGCTGCATCCAGGAGT

ATTCAGACCAGCTCAGCTCTTCAACATGACAGTCTGTTCGTTCATCGTGATACTCCTGAGGACAACCG

TGATATCCCGTTCGAGTTTTCAGAGGCCAACAAGAAGAGAGTGGAAGCCTTACTAGGAATCCATCCT

GAAGGCCACAAGCGTGGTGCCATGATCCCACTGCTCGACCTGGCTCAGCGTCAGGCTGGAGGTTGG

CTGCCGATATCTGCCATGCATAAAGTAGCTGAAATCCTCAAACTTCCTCGCATGAGAGTTTATGAGGT

TGCTACGTTCTACACTATGTTTATTAGACGACCAATCGGCAAGTACCATATCCAAGTTTGCACGACAA

CTCCTTGCTGGCTCCGAGGTTCTGATGCTATCCTGAAAGCTCTCACTGAGGGTACACAATGCCATGT

TGGAGGAAACAGCCCTTGTGGCAAGTTCTCTATTTCTGAGGTTGAATGCCTTGGTGCCTGTGTTAAT

GCTCCTATGATTCAAGTCAACGATGATTACTACGAAGACCTGTCAGTAGATGACACAAAGGAAATTAT

TGAAAAGCTCAAAAGGGACGAGAAACCGAAAGCTGGCCCTAGGAGCGGCAGATTCGCCTCAGAACCC

TTGGGAGGACTCACTTCTCTCACCGAAGAACCTACAGGCCCCGGTTTTGGACTACAACCCGGCCTCA

AGGCCTAGAACAAAAGTTTCCGTTTTGTAAATTTTATTTATAGGCAATATTTAAATAAATCATGTTA

GAATCGTAAAAAAAAAAAAAAAAAAAA

SEQ ID NO: 45 (WXM-corn, NADH dehydrogenase ubiquinone flavoprotein 2 ubiquinone flavoprotein 2, GenBank: GH999345)
GCACGAGGCGCTTGTTCGCGAACAGTGTTTCGCAATAACTTTTATAAAAATTACAAGAAAACAACAGT

AAATCATGTTGTCCAGCCTCAGAACTGGAGTTCAGGGCTTGTGGCGCACTACTTCCAGGGCCCTGCA

GACCAGCTCGACCCTGCAACATGACAGTCTTTTCGTCCACCGAGACACCCCTGAGGACAACCCTAACA

-continued

```
TACCGTTCGAGTTTACCCCACAGAACCAAAAGAGGGTGGAAGCACTCCTAGCAATTTATCCCGAAGG

ACACAAGAGAGGTGCCATGATTCCTCTACTGGACTTGGCCCAGCGTCAGGCAGGAGGCTGGCTGCCA

ATCTCCGCGATGCACAAAGTAGCGGAAGTCCTCAATTTACCTCGCATGAGAGTCTACGAAGTAGCTA

CATTCTACACCATGTTTATTAGGAGACCAATAGGCAAATACCACGTCCAAGTGTGCACAACCACTCCT

TGCTGGCTGAGGGGCTCGGACGCTGTGCTGAACGCTATCAAGGAAGCAACTGGCTGTGAAGTTGGA

GGCAACAGCCCTTGCGGAAAATTCTCCATTTCTGAGGTTGAATGTCTTGGAGCCTGTGTCAACGCAC

CAATGATTCAAGTTAACGATGACTATTATGAGGACCTGTCCGTTGAAGACACAAAGGAAATTATCGAA

AAGCTAAAGAAAGACGAAAAACCATTACCGGGTCCCAGAAGCGGCAGGTTCGCATCCGAGCCTCTGG

GAGGGCTCACGTCCCTCACGGAAGAACCCACGGGCCCCGGCTTCGGCGTACAAGACGCCCTGAAGGC

CTAGGCAGATGTACATTGTTTTGTAATTTTATTTCATAGGTATTTAATAAATCATGTTAGATC

SEQ ID NO: 46 (TRV1, 29 KD protein, GenBank: AF166084)
   TGGAAGACAAGTCATTGGTCACCTTGAAGAAGAAGACTTTCGAAGTCTCAAAATTCTCAAATCT

AGGGGCCATTGAATTGTTTGTGGACGGTAGGAGGAAGAGACCGAAGTATTTTCACAGAAGAAGAGAA

ACTGTCCTAAATCATGTTGGTGGGAAGAAGAGTGAACACAAGTTAGACGTTTTTGACCAAAGGGATT

ACAAAATGATTAAATCTTACGCGTTTCTAAAGATAGTAGGTGTACAACTAGTTGTAACATCACATCTA

CCTGCAGATACGCCTGGGTTCATTCAAATCGATCTGTTGGATTCGAGACTTACTGAGAAAAGAAAGA

GAGGAAAGACTATTCAGAGATTCAAAGCTCGAGCTTGCGATAACTGTTCAGTTGCGCAGTACAAGGT

TGAATACAGTATTTCCACACAGGAGAACGTACTTGATGTCTGGAAGGTGGGTTGTATTTCTGAGGGC

GTTCCGGTCTGTGACGGTACATACCCTTTCAGTATCGAAGTGTCGCTAATATGGGTTGCTACTGATT

CGACTAGGCGCCTCAATGTGGAAGAACTGAACAGTTCGGATTACATTGAAGGCGATTTTACCGATCA

AGAGGTTTTCGGTGAGTTCATGTCTTTGAAACAAGTGGAGATGAAGACGATTGAGGCGAAGTACGAT

GGTCCTTACAGACCAGCTACTACTAGACCTAAGTCATTATTGTCAAGTGAAGATGTTAAGAGAGCGTC

TAATAAGAAAAACTCGTCTTAA
```

Example 2, Isolation of Gene Fragments of Trypsin Precursor, Dopa Decarbxylase, Etc Using *Helicoverpa armigera* cDNA library (ZAP express) (cDNA library was constructed based on total RNA extracted from the midguts of 5-instar *H. armigera* larvae fed with artificial diet containing 1 mg g$^{-1}$ gossypol for one day) as template, fragments of trypsin precursor, dopa decarboxylase were amplified via PCR and corresponding fragments were used to produce dsRNA expression vectors. PCR Reaction solution is: 5 μL 10× buffer solution, 2.5 μL 10 mM dNTP, 2 μL primer F, 2 μL primer R, 2 μL cDNA, 1 μL pfu enzyme, add water to a total volume of 50 μL, PCR condition is 94° C. 4 min, 94° C. 30 s, 55° C. 30S, 72° C. 2 min, 30 cycles, 72° C. 10 min. DNA fragments with expected size are collected after electrophoresis of PCR products.

Using *Helicoverpa armigera* wxm-12 (NADH dehydrogenase ubiquinone flavoprotein 2) as template, corresponding cDNA sequence of *Ostrinia nubilalis* was obtained via homology search against *Ostrinia nubilalis* EST data base, and was named as wxm-corn. Use bio-synthesized *Ostrinia nubilalis* EST as template, to carry out PCR amplification, and the PCR amplified product was used to construct dsRNA expression vectors and VIGS vectors. The PCR conditions are the same as above.

Gene-specific primers are as follows:

WXM-2, Trypsin Precursor:

```
                              (SEQ ID NO: 7)
wxm-2-F-BamHI:   CGGGATCCACCCTACTATTGCGGCTCTT (SEQ ID NO: 8)
wxm-2-R-XbaI:    CGTCTAGAAGGAGCAGACACCGACAA (SEQ ID NO: 9)
wxm-2-F-SacI:    CGGAGCTCACCCTACTATTGCGGCTCTT (SEQ ID NO: 10)
wxm-2-R-NotI:    CGGCGGCCGCAGGAGCAGACACCGACAA
```

WXM-6, Dopa Decarboxylase:

```
                              (SEQ ID NO: 11)
wxm-6-F-BamHI:   CGGGATCCTGTATGGCGTGGAGAATC (SEQ ID NO: 12)
wxm-6-R-XbaI:    CGTCTAGACAGCAGCAGCCTTTACTT (SEQ ID NO: 13)
wxm-6-F-SacI:    CGGAGCTCTGTATGGCGTGGAGAATC (SEQ ID NO: 14)
wxm-6-R-NotI:    CGGCGGCCGCCAGCAGCAGCCTTTACTT
```

WXM-12, NADH Dehydrogenase Ubiquinone Flavoprotein 2 wxm-12-F-BamHI:  CGGGATCCCAACAAGAAGAGAGTGGAAGC (SEQ ID NO: 15)

wxm-12-R-XbaI:  CGTCTAGATTTCGGTTTCTCGTCCCT (SEQ ID NO: 16)

wxm-12-F-SacI:  CGGAGCTCCAACAAGAAGAGAGTGGAAGC (SEQ ID NO: 17)

wxm-12-R-NotI:  CGGCGGCCGCTTTCGGTTTCTCGTCCCT (SEQ ID NO: 18)

WXM-E Myosin Heavy Chain, Isoform B wxm-E-F-BamHI:  CGGGATCCGAGGACCGCAAGAACCAC (SEQ ID NO: 19)

wxm-E-R-XbaI:  CGTCTAGATGGGAAGGTGCCGAAA (SEQ ID NO: 20)

wxm-E-F-SacI:  CGGAGCTCGAGGACCGCAAGAACCAC (SEQ ID NO: 21)

wxm-E-R-NotI:  CGGCGGCCGCTGGGAAGGTGCCGAAA (SEQ ID NO: 22)

WXM-25, ATP Synthase Beta wxm-25-F-BamHI:  CGGGATCCCTACCTTGCTGTGAACCCTC (SEQ ID NO: 23)

wxm-25-R-XbaI:  CGTCTAGAAATGGTGCCTGCCTCAAC (SEQ ID NO: 24)

wxm-25-F-SacI:  CGGAGCTCCTACCTTGCTGTGAACCCTC (SEQ ID NO: 25)

wxm-25-R-NotI:  CGGCGGCCGCAATGGTGCCTGCCTCAAC (SEQ ID NO: 26)

NADH dehydrogenase ubiquinone flavoprotein 2, the second region of WXM-12, WXM-12 (501):

wxm-12(501)-F-BamHI:  CGGGATCCACCAATCGGCAAGTACCATA (SEQ ID NO: 47)

wxm-12(501)-R-XbaI:  CGTCTAGAAACGGAAACTTTTTGTTCTAGG (SEQ ID NO: 48)

NADH dehydrogenase ubiquinone flavoprotein 2, homologous genes of WXM-12 in *Ostrinia nubilalis* (WXM-corn):

wxm-corn-F-BamHI:  CGGGATCCCTAGCAATTTATCCCGAAGG (SEQ ID NO: 49)

wxm-corn-R-XbaI:  CGTCTAGACAGGTCCTCATAATAGTCATCG (SEQ ID NO: 50)

Example 3, Vector Construction and *Agrobacterium tumefaciens*-Mediated Transformation 1. Vector Construction Structures of dsRNA vectors were as shown in FIG. 1A, including plant expression promoter CaMV35S promoter, a forward (i.e., Sense, S) gene fragment, an *Arabidopsis thaliana* RTM gene intron (i.e., Intron, about 128 bp), a reverse (i.e., Antisense, AS) gene fragment and NOS terminator. They were obtained by inserting sequence containing Sense-Intron-Antisense into between BamHI and SacI sites on pCambia2301 vector (purchased from Cambia).

Using *Arabidopsis thaliana* genome as template, first, use specific primers RTM+ (5'-TCTAGAACGTTGTAAGTCT-ATTTTTG-3' (SEQ ID NO: 27)) and RTM− (5'-GCGGC-CGCTCTGCTGGGTCCAAATCACA-3' (SEQ ID NO: 28)) containing XbaI and NotI to amplify the intron (about 128 bp) of *Arabidopsis thaliana* RTM gene (AT2G43730) using high fidelity enzyme pfu for PCR amplification, using restriction enzymes XbaI and NotI to double digest the PCR products, and cloned between Xbat and NotI at the multiple cloning sites of pBSK (purchased from Clontech).

Using *Helicoverpa armigera* cDNA library as template and individual gene-specific primer pairs containing restriction enzyme NotI and SacI cutting sites as listed in Example 2 (for example, wxm-12-F-SacI and wxm-12-R-NotI to amplify NADH dehydrogenase ubiquinone flavoprotein 2; wxm-6-F-SacI and wxm-6-R-NotI to amplify dopa decarboxylase, etc.) with high fidelity enzyme pfu for PCR amplification, cloned to obtain corresponding fragments, using NotI and SacI to double digest the PCR products, and respectively inserted between the cloning sites (NotI/SacI) on pBSK vector containing RTM intron.

In the same way, using individual gene-specific primer pairs containing restriction enzyme BamHI and XbaI cutting sites as listed in Example 2 (for example, wxm-12-F-BamHI and wxm-12-R-XbaI for amplifying NADH dehydrogenase ubiquinone flavoprotein 2; wxm-6-F-BamHI and wxm-6-R-XbaI for amplifying dopa decarboxylase, etc.) with high fidelity enzyme pfu for PCR amplification, respectively cloned the obtained fragments between BamHI and XbaI cloning sites of the above-mentioned pBSK inserted with reverse (AS) fragments, to obtain double-stranded RNA vectors.

Using HindIII and BamHI to splice CaMV35S promoter from pBI121 vector (purchased from Clonetech), using SacI and EcoRI to splice NOS terminator, and separately inserted into HindIII/BamHI sites, and SacI/EcoRI sites of pCAM-BIA2301 vector, to obtain vector containing CaMV35S-NOS, named as p35SNOS.

Double digesting the constructed double-stranded RNA vectors with BamHI and SacI, meanwhile, double digesting p35SNOS vector with BamHI and SacI, inserting the enzyme-spliced double-stranded fragments between BamHI and SacI, and respectively named as dstrypsin/2301, dsdopa/2301, dsNADH/2301 and ds ATP synthase beta/2301 and ds Myosin heavy chain/2301.

2. Construction of Viral Vectors of Dswxm-12/TRV2, Dswxm-12(501)/TRV2 and dswxm-corn/TRV2

Figure 1B:
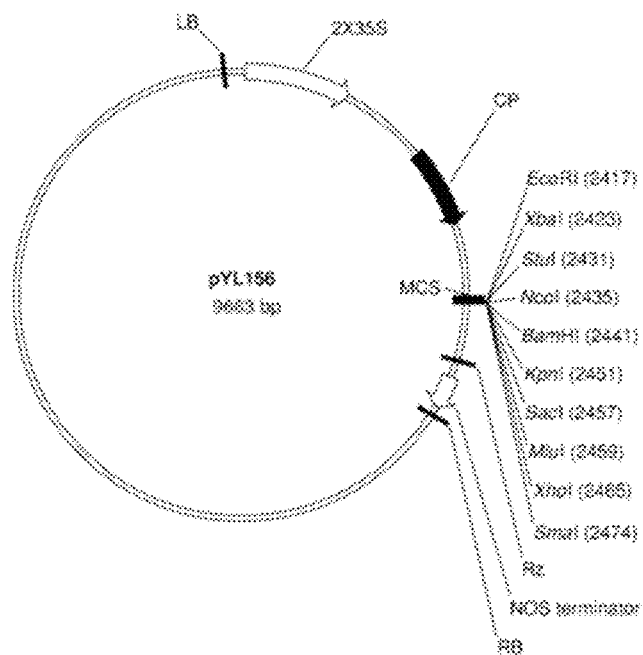

Preparing virus vectors targeting the WXM-12, WXM-12(501) and dswxm-corn sequences. Using gene-specific primer pairs containing restriction enzyme BamHI and XbaI cutting sites as listed in Example 2 (such as wxm-12(501)-F-BamHI: CGGGATCCACCAATCGGCAAGTACCATA (SEQ ID NO: 51) and wxm-12(501)-R-XbaI: CGTCTA-GAAACGGAAACTTTTTGTTCTAGG (SEQ ID NO: 52)) to obtain target fragments by PCR amplification. Recover target fragments, and double digest them with BamHI and XbaI. Ligate the recovered double-digested product fragments with pYL156 vector (FIG. 1B, obtained from Zhejiang University), to obtain target vectors, and named as dswxm-12/TRV2, dswxm-12(501)/TRV2 and dswxm-corn/TRV2, respectively.

2. *Agrobacterium tumefaciens*-Mediated Transformation

*Agrobacterium tumefaciens*-mediated transformation was performed via freezing and thawing method. Conventional *Agrobacterium tumefaciens* LBA4404 (referred to U.S. Pat.

No. 7,321,031) may be used as *Agrobacterium* strain. Place said constructed plant expression vector and 50 μl/tube competent cells on ice for 30 minutes and quickly freeze in liquid nitrogen for 1 minute. Melt the bacteria solution in water bath at 37° C. for 5 minutes, add 1 ml LB culture medium, 28° C., 220 rpm, and incubate for 2-4 hours. Take 50~100 μl and spread on the LB culture medium (25 mg/L rifampicin, 50 mg/L kanamycin and 100 mg/L streptomycin), 2 days later, select single bacterial colony for PCR detection.

Example 4, Screening for Genetically Transformed Plants and Transgenic Progenies 1, *Arabidopsis thaliana* Transformation and Screening

*Arabidopsis thaliana* (Col0) is transformed via floral dip method (Clough and Bent, 1998, Plant J. 16, 735-743). Inoculate a single bacterial colony LBA4404, containing binary vector in 3 ml LB culture medium (containing 25 μg/ml Rif, 25 μg/ml Str and 50 μg/ml Kan), grow at 28° C., 220 rpm, for 12 hours. Inoculate the bacterial solution in 50 ml LB culture medium (25 μg/ml Rif, 25 μg/ml Str and 50 μg/ml Kan), grow at 28° C., 220 rpm, for 12 hours. Inoculate 50 ml bacterial solution in 250 ml LB culture medium (25 μg/ml Rif, 25 μg/ml Str and 50 μg/ml Kan), grow at 28° C., 220 rpm, for 12 hours.

Centrifuge bacteria solution at 5000 rpm, room temperature for 5 minutes, and remove supernatant. Resuspend the bacteria in 300 ml of 5% sucrose solution containing 0.02% Silwet L-77. Soak floral part of *Arabidopsis thaliana* plant clones in bacteria solution for 5 seconds, lay inside plastic containers, keep moisted, keep in dark for 16-24 hours, then grow in greenhouse until blossom and produce seeds.

Vernalize the harvested seeds of $T_0$ generation at 4° C. for 2 days. Treat with 20% bleaching water for 15 minutes, wash with sterile water for 3-4 times. Resuspend the seeds in 0.5% agarose (55° C.), spread on 0.8% agar-containing MS culture medium (containing 50 μg/ml Kan) at 22° C., grow under the condition of continuous lighting for about 1 week. Grow resistant green sprouts transplanted to nutrient soil (peat:vermiculite:perlite=1:1:1).

2, Cotton Transformation and Screening

*A. tumefaciens* containing dswxm-12/2301 plasmid was cultured on YEB medium (kanamycin 50 mg/L, rifampicin 25 mg/L and streptomycin 25 mg/L) for 2-3 days. Single bacterial colone was inoculated in YEB liquid culture medium containing the same antibiotics, and incubated in shaker at 200 rpm, 28° C. overnight. After centrifuge at 4000 rpm for 10 min, precipitate was re-suspended with ½ MS liquid medium containing glucose 30 g/L and acetosyringone 100 μmol/L, adjust $OD_{600}$ to about 0.4-0.6, and serve as ready for use infection solution.

Cotton R15 (conventional upland cotton, originated from Cotton Research Institute, Shanxi Academy of Agricultural Sciences, referring to Shangguan Xiaoxia, Li Yane, Liang Yunsheng, Wu Xia, Du Qiufang, Zhang Linshui, Correlation between Expression of GUS Gene and NPTII Gene and Their Application in the Detection of Transgenic Cotton, Cotton Science 2007 19(3)). Place seeds, after routinely disinfection, on ½ MS0 culture medium (½MS salt+5 g/L glucose+7 g/L agar powder, pH 6.0), culture and germinate in the dark, after 5-7 days, cut the hypocotyl of disinfected seedling into fragments with about 1.0 cm, and serve as ready for use transgenic explants.

Soak and infect the explants in *Agrobacterium tumefaciens* solution for 15-20 minutes, transfer to co-culture medium MSB1 (MS salt+B5 organic+30 g/L glucose+0.1 mg/L KT+0.1 mg/L 2,4-D+2.2 g/L Gelrite, pH 6.0), after 2 days culture in dark under 22° C., transfer the explants to culture medium MSB2 (MSB1+500 mg/L cephalosporin+80 mg/L kanamycin) to induce callus. After the explants induced by callus resistance, proliferation of callus and embryogenic callus (culture medium MSB3: MS salt+B5 organic+30 g/L glucose+2.5 g/L Gelrite, pH 6.0), somatic embryogenesis occurs (culture medium MSB4: MS salt+B5 organic+30 g/L glucose+1.0 g/L asparaginic acid+2.0 g/L glutamine+3.0 g/L Gelrite, pH 6.0; double the amount of KNO3 in MS salt, and remove NH4NO3), regenerate resistant test-tube plantlets. When the test-tube plantlets grow to 3-4 true leaves, transplant to flowerpots, and grow in artificial climate chambers.

After screening, transforming cotton with dswxm-12/2301 vectors yields 11 strains and 15 transgenic plants capable of producing seeds.

3, Tobacco VIGS Infection

Use Tobacco Rattle Virus (TRV) system obtained from Zhejiang University, including pYL156, pTRV1 viral vectors, and control PDS/TRV2 vectors described in Example 3. Application of the present system refers to Current Protocols in Microbiology (2006) 16I.6.1-16I.6.13. Tobacco rattle virus RNA-1 complete sequence (TRV1, GenBank: X06172.1; *Nicotiana benthamiana* phytoene desaturase (PDS) complete cds GenBank: EU165355.1).

Culture *Agrobacterium tumefaciens* carrying pTRV1 with, respectively, single clone of *Agrobacterium tumefaciens* containing dswxm-12/TRV2, dswxm-12(501)/TRV2, dswxm-corn/TRV2 and control PDS/TRV2 in LB liquid culture medium (25 mg/L rifampicin, 50 mg/L kanamycin and 25 mg/L streptomycin) overnight, use VIGS transfectant liquid (10 mM MES, 10 mM magnesium chloride, 0.1 mM acetosyringone) to adjust OD to 2.0. After still standing at room temperature for 4-6 hours, mix TRV1 and *Agrobacterium tumefaciens* containing pTRV2 target gene at 1:1 ratio, and use injector for infiltration injection on tobacco leaves. After culturing the inoculated tobacco at 21° C. for 7 days, use *Agrobacterium tumefaciens* containing tobacco PDS gene as positive control (whiting of newly-grown leaves), to determine infection stage and infection efficiency. The newly-grown leaves of tobacco infected by control PDS/TRV2 virus turn white (indicating successful infection). Use newly-grown leaves of tobacco infected by dswxm-12/TRV2, dswxm-12(501)/TRV2, and dswxm-corn/TRV2 viruses for insect tests.

Example 5, Molecular Identification of Transgenic Plants

1. Identification of Transgenic *Arabidopsis thaliana*

In this example, regarding each of the prepared vectors mentioned above (dstrypsin/2301, dsdopa/2301, dsNADH/2301, ds ATP synthase beta/2301 and ds Myosin heavy chain/2301), through screening, obtained more than 10 clones of transgenic *Arabidopsis thaliana* clones in Example 3 (each clone named: dsNADH dehydrogenase ubiquinone flavoprotein 2, ds trypsin precursor, ds dopa decarboxylase, ds ATP synthase beta and ds Myosin heavy chain; and relating to same type of plant clones sequentially indicated by −1, −2 . . . ) and used GUS staining method to verify plant clones. Because pCAMBIA 2301 vector itself carries GUS gene, therefore, by detecting the presence of GUS in plant clones, identification results can be obtained.

Plant materials are soaked in GUS staining solution, at 37° C. for 12-24 hours. De-stained in 70% ethanol, and preserved in 70% ethanol. GUS staining solution (100 mM pH7.0 phosphate buffer, 5 mM K3[Fe(CN)6], 5 mM K4[Fe(CN)6], 10 mM EDTA, 1 mM X-gluc, 0.1% Triton X-100)₀ ₀

2, Identification of Transgenic Cotton

DNA extraction is performed with the following method: measure 0.5 g of transgenic cotton leaves, grind them to powder in liquid nitrogen, transfer the powder into a 8 ml centrifuge tube, add 5 ml of grinding buffer (1 M glucose, 0.1 M citric acid, 5% Triton X-100 (pH 5.0)), and mix it well. Centrifuge the mixture at 1000 g for 10 min at 22° C., collect the precipitation, resuspend it in the grinding buffer, and centrifuge again. Repeat the processes 3 times until grayish-white precipitates appear. Wash the precipitates with 5 ml washing buffer (0.5 M glucose, 0.05 M citric acid (pH 5.0)). Centrifuge the mixture at 1000 g for 10 min at 22° C., and remove the supernatant. Repeat the processes for 2-4 times until the precipitates are milk white. Add 5 ml of lysis buffer (1% SDS, 1.4 M NaCl, 0.1 M EDTA (pH 8.3)), and lyse the precipitates in a 60° C. water bath for 15 min. Centrifuge at 5000 g for 10 min at 22° C., and collect the supernatant. Add twice volumes of anhydrous ethyl alcohol, and centrifuge at 10,000 g for 5 min at 4° C. Discard the supernatant, blow-dry the precipitates, dissolve the precipitates in 2 ml 0.1×SSC solution, and centrifuge the solution to remove the insoluble after sufficient dissolution. Add NaCl to obtaining a final concentration of 1M (about 0.058 g NaCl/ml 0.1×SSC (0.015 M NaCl, 0.015M sodium citrate)). Add equal volume of chloroform:isopentyl alcohol (24:1) and mix well. Centrifuge the solution at 12,000 rpm for 10 min at 4° C. and collect the supernatant. Repeat the extraction one more time. Add twice the volume of anhydrous ethyl alcohol to the supernatant, allow it to stand at −20° C. for 10 min, and centrifuge it at 12,000 rpm for 10 min at 4° C. Dissolve the precipitates in 0.1×SSC. Measure the ratio of OD 260/280, which usually is in the range of 1.8-2.0. Concentration (g/ml) of DNA=50×A260× dilution factor.

Primers for PCR detection are wxm-12-F and wxm-12-R. Their sequences are:

```
                            (SEQ ID NO: 15)
wxm-12-F-BamHI:    CGGGATCCCAACAAGAAGAGAGTGGAAGC (SEQ ID NO: 16)
wxm-12-R-XbaI:     CGTCTAGATTTCGGTTTCTCGTCCCT
```

PCR reaction conditions are: initial denaturation for 5 min at 94° C.; then pre-denaturation for 30 s at 94° C., renaturation for 30 s at 55° C., extension at 72° C. for 30 s, for a total of 30 cycles. The final extension was at 72° C. for 10 min. The amplified fragment is about 500 bp in size.

Figure 3A:
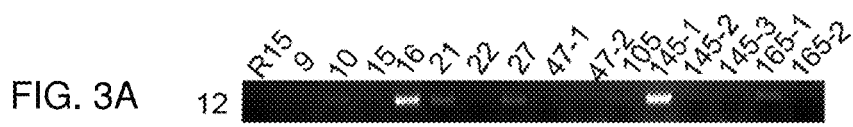
FIGS. 3A to 3C show PCR and RT-PCR analysis of dsWXM-12 transgenic cotton plants.

FIG. 3A shows results of DNA analyses of transgenic cottons (R15, 9, 10, 15, 16, 21, 22, 27, 145-1, 145-2, 145-3, 165-1, 165-2) containing dswxm-12/2301. R15 is an acceptor material of transgenic cotton. Lanes with specific bands indicate cottons containing the dswxm-12/2301vector.

Example 6: Assessing the Expression Levels of Double-Stranded RNAs

1, Extraction of *Arabidopsis thaliana* RNA

Take transgenic *Arabidopsis thaliana* material (about 100 mg) and grind it thoroughly in liquid nitrogen. Transfer it to a 1.5 ml centrifuge tube, add 1 ml of Trizol (Invitrogen, Cat. 15596-018), mix well, and allow it to stand at room temperature for 5 minutes. Add 200 µL of trichloromethane, mix well and centrifuge it at 12,000 rpm for 10 min. Collect the supernatant and add 500 µL of isopropanol to the supernatant, mix well, and centrifuge it at 12,000 rpm for 10 min. The precipitates are washed with 70% ethanol, dried under vacuum, and dissolve in 20-50 µL H₂O (RNase free).

2, Extraction of Cotton RNA

Methods for the extraction of cotton RNA are as follows: grind the cotton material in liquid nitrogen, add 1 ml of preheated RNA extracting solution to each 200 mg of material (0.2 M Tris, pH 8.0, 50 mM EDTA, 1 M NaCl, 1% CTAB and 1% β-mercaptoethanol), and keep at 65° C. for 30 minutes. Add 0.6 ml of chloroform and extract twice. Add LiCl to the supernatant to a final concentration of 2 M. Allow it to stand at −20° C. for 3 hours. Centrifuge at 13000 g for 10 min. The precipitates are washed with 70% ethanol once, dissolved in water, and stored at −20° C.

3, Extraction of Tobacco RNA

Methods for the extraction of tobacco RNA are as follows: grind the new leaves of tobacco infected by the virus in liquid nitrogen, add 1 ml of 65° C. preheated RNA extracting solution to each 200 mg of materials (0.2 M Tris, pH 8.0, 50 mM EDTA, 1 M NaCl, 1% CTAB and 1%/3-mercaptoethanol), and allow it to sand at 65° C. for 30 minutes. Add 0.6 ml of chloroform and extraction twice. Add LiCl to the supernatant to a final concentration of 2 M. Allow it to stand at −20° C. for 3 hours, and centrifuge at 13000 g for 10 min. The precipitates are washed with 70% ethanol once, dissolved by adding water, and stored at −20° C.

4, Northern Blot Analysis of the Expression Levels of Double-Stranded RNAs

Add 5×RNA sample buffer and 10×RNA (formaldehyde) electrophoresis loading buffer to the RNA sample. Mix it well, keep it at 65° C. for 10 min, and then cool it on ice. The amount of sample added to each lane is 15 µg total RNA, and run electrophoresis on formaldehyde denaturing gel. The electrophoresis uses denaturing agarose gel, 1×MOPS electrophoresis buffer solution, the electric field strength is 8 V/cm. Electrophoresis is stopped when bromophenol blue dye moves to ⅔ of the gel length. Use ddH₂O to wash the gel, and then allow it to equilibrate in 20×SSC for 40 min. Build a transfer platform, and transfer the RNA to Hybond-XL (Amersham, Cat.RPN303S) nylon membrane (about 18 h) by the capillary method in 10×SSC transfer buffer. After the transfer, mark the wells' positions in membrane with a pencil, and cut the top left corner as a maker. The membranes are washed briefly with 6×S SC solution, UV cross linked (120 mJ), put between two pieces of filter papers and baked at 80° C. for 2 h. The membranes are sealed and saved for later use.

Label of probe: measure 25 ng purified PCR product as a template for labeling (use primers wxm-12-F and wxm-12-R to amplify the fragment of NADH dehydrogenase ubiquinone flavoprotein 2. The length of probe is 475 bp. Use primers wxm-2-F and wxm-2-R to amplify the fragment of trypsin precursor). Use the Prime-a-Gene Labeling System (Promega, Cat.U1100) to label the probes, in a 37° C. water bath for 1 hour. The labeled probes are put in boiling water for 5 min and then immediately placed on ice for later use.

Pre-hybridization and hybridization are performed with the ExpressHyb system of Clontech: place a nylon membrane in a hybridization tube, wet it with 6×SSC, and make sure there is no bubble between the membrane and tube wall. Discard the 6×SSC buffer and add 5 nil hybridization solution. Pre-hybridization is performed for 60 min at 37° C. After pre-hybridization, replace the hybridization solution with 5 ml fresh hybridization solution, add the probe, mix and allow it to hybridize overnight.

Wash the membrane and tablet: after hybridization, discard the hybridization solution. Wash the membrane twice with 2×SSC, 0.05% SDS, 5 minutes each time. The membrane is further washed twice with 0.2×SSC, 0.1% SDS, 20 minutes each time. The membrane is wrapped with a plastic film and fixed with a tape. An intensifying screen and an X-ray film are pressed against the membrane and left at −70° C. for 2 days. The film was developed with D-72 developing solution.

Figure 2A:
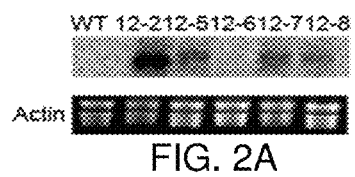
FIGS. 2A to 2F show northern blot or RT-PCR analysis of dsRNA abundances of target genes in transgenic *Arabidopsis thaliana* (trypsin precursor gene, dopa decarboxylase gene, NADH dehydrogenase ubiquinone flavoprotein 2 gene, ATP synthase beta subunit gene, and myosin heavy chain isoform B gene).

FIG. 2A shows results of Northern blot analysis of expression levels of NADH dehydrogenase ubiquinone flavoprotein 2 dsRNA in transgenic *Arabidopsis thaliana*. WT represent the wild-type plant control, and the lanes with bands represent the expression of dsRNA in the corresponding plants.

5. RT-PCR Detection of the Expression Levels of Double-Stranded RNAs

Properly dilute the RNA sample with RNase-Free water, and measure the UV absorption value at wavelengths between 200 nm-300 nm. RNA concentration=40 μg/ml× A260×dilution factor. Use RNA PCR Kit (Takara) to perform reverse transcription. The reaction system is as described in the instructions for the kit. Add 1 μg total RNA into a 20 μL reaction system, and perform the reaction for 40 minutes at 42° C. to synthesize the first strand. PCR reaction system is as follows: 2 μL 10× buffer, 0.5 μL 10 mM dNTP, 1 μL primer F, 1 μl primer R, 0.5 μL cDNA, 0.2 L ExTaq enzyme, and water is added to make the volume 20 μL. PCR reaction conditions are: 94° C., 4 min; 94° C., 30 s; 55° C., 30 s; 72° C., 30 s; for 30 cycles, followed by 72° C., 10 min. The products of PCR are detected with electrophoresis. Sequences of primer F and primer R that correspond to each gene are shown in table 3.

Figure 2B:
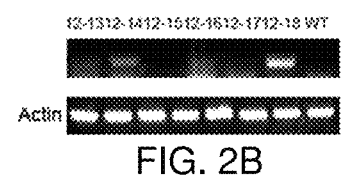

FIG. 2B shows results of RT-PCR detection of the expression levels of dsRNA containing the NADH dehydrogenase ubiquinone flavoprotein 2 sequence in transgenic *Arabidopsis thaliana*. WT represent the wild-type plant control, and the lanes with specific bands represent expression of the dsRNA in the corresponding plant.

Figure 2C:
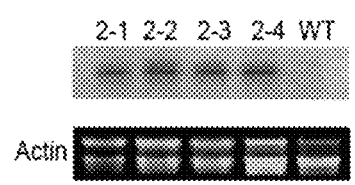

FIG. 2C shows Northern blot analysis of the expression levels of dsRNA containing the trypsin precursor sequence in transgenic *Arabidopsis thaliana*. WT represents the wild-type plant control, and the lane with bands represent expression of the dsRNA in the corresponding plants.

Figure 2D:
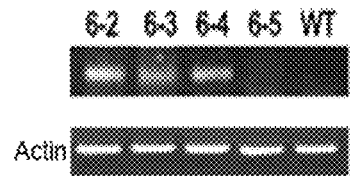

FIG. 2D shows results of RT-PCR detection of the expression of transgenic *Arabidopsis thaliana* containing dopa decarboxylase. WT represents the wild-type plant control, and the lanes with specific bands represent expression of the dsRNA in the corresponding plants.

Figure 2E:
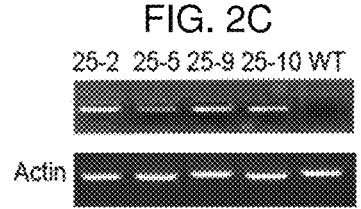

FIG. 2E shows results of RT-PCR detection of the expression of transgenic *Arabidopsis thaliana* containing ATP synthase beta. WT represents the wild-type plant control, and the lanes with specific bands represent expression of the dsRNA in the corresponding plants.

Figure 2F:
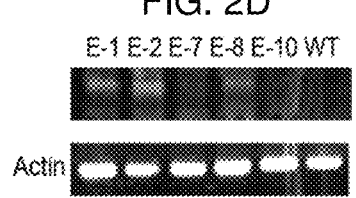

FIG. 2F shows results of RT-PCR detection of expression of transgenic *Arabidopsis thaliana* containing Myosin heavy chain. WT represents the wild-type plant control, and the lanes with specific bands represent expression of the dsRNA in the corresponding plants.

Figure 3B:
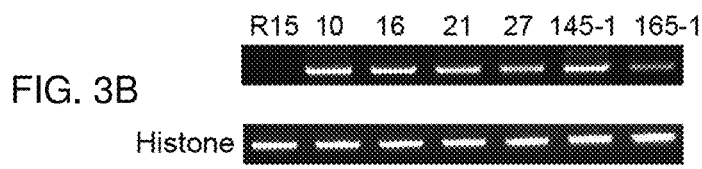

FIG. 3B shows results of RT-PCR detection of expression of transgenic cotton (10, 16, 21, 27, 145-1, 165-1) containing NADH dehydrogenase ubiquinone flavoprotein 2. The lanes with specific bands represent expression of the dsRNA in the corresponding plants.

TABLE 3

Information of primers for each gene

| Gene name | Primer name | SEQ ID NO: | Primer sequence |
|---|---|---|---|
| trypsin precursor | wxm-2-F | 29 | ACCCTACTATTGCGGCTCTT |
|  | wxm-2-R | 30 | AGGAGCAGACACCGACAA |
| dopa decarboxylase | wxm-6-F | 31 | TGTATGGCGTGGAGAATC |
|  | wxm-6-R | 32 | CAGCAGCAGCCTTTACTT |
| NADH dehydrogenase ubiquinone flavoprotein 2 | wxm-12-F | 33 | CAACAAGAAGAGAGTGGAAGC |
|  | wxm-12-R | 34 | TTTCGGTTTCTCGTCCCT |
| Myosin heavy chain, isoform B | wxm-25-F | 35 | CTACCTTGCTGTGAACCCTC |
|  | wxm-25-R | 36 | AATGGTGCCTGCCTCAAC |
| ATP synthase beta | wxm-E-F | 37 | GAGGACCGCAAGAACCAC |
|  | wxm-E-R | 38 | TGGGAAGGTGCCGAAA |
| NADH dehydrogenase ubiquinone flavoprotein 2 | wxm-12(501)-F | 39 | ACCAATCGGCAAGTACCATA |
|  | wxm-12(501)-R | 40 | AACGGAAACTTTTTGTTCTAGG |
| NADH dehydrogenase ubiquinone flavoprotein 2 from *Ostrinia nubilalis* | wxm-corn-F | 41 | CTAGCAATTTATCCCGAAGG |
|  | wxm-corn-R | 42 | CAGGTCCTCATAATAGTCATCG |
| TRV1, 29KD protein | TRV1-F | 43 | CTTGAAGAAGAAGACTTTCGAAGTCTC |
|  | TRV1-R | 44 | CAACCCACCTTCCAGACA |

Figure 3C:
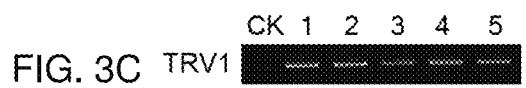
Figure 4A:
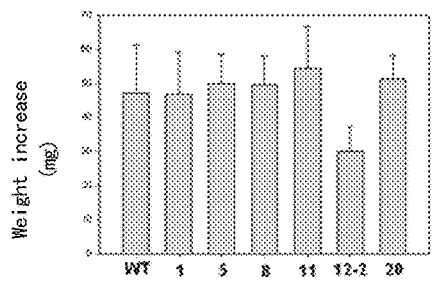
FIGS. 4A to 4E show body weights of *H. armigera* after feeding on transgenic *Arabidopsis* for 3-7 days.
Figure 4B:
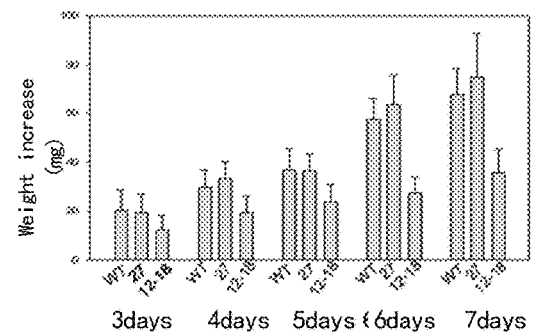
Figure 4C:
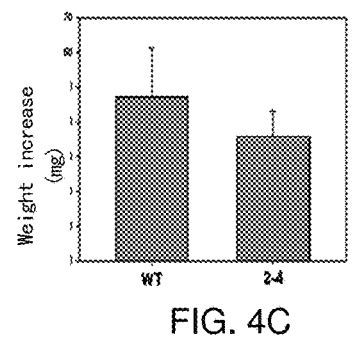
Figure 4D:
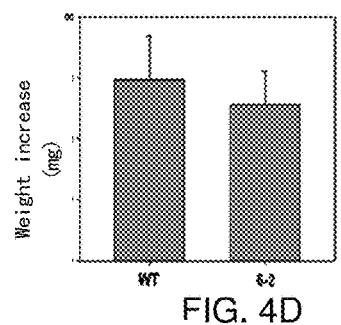
Figure 4E:
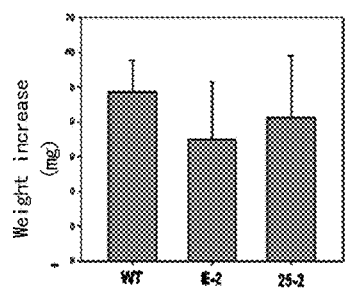
Figure 5A:
FIGS. 5A to 5C show expression status of *H. armigera* target genes after feeding on transgenic *A. thaliana* for 3-7 days.
Figure 5B:
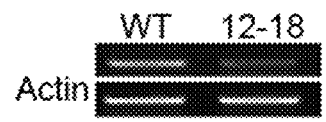
Figure 5C:
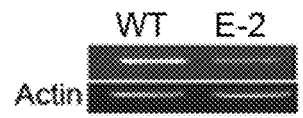

FIG. 3C shows results of RT-PCR detection of five random tobaccos infected by viruses (CK, 1, 2, 3, 4, 5). The lanes with specific bands represent expression of the TRV1 in the corresponding plants.

Example 7, Detection of the Effects of Transgenic Plants Expressing dsRNA on the Growth of *Helicoverpa armigera* and *Ostrinia furnacalis*

1. Extraction of RNA from *Helicoverpa armigera* and *Ostrinia furnacalis*

Take midgut of *Helicoverpa armigera* or *Ostrinia furnacalis* (about 100 mg) and put it into liquid nitrogen and grind. Transfer the powder to a 1.5 ml centrifuge tube, add 1 ml trizol (Invitrogen, Cat.15596-018), mix well and keep at room temperature for 5 min. Centrifuge at 12,000 rpm for 10 min, and discard the precipitates. Add 200 µL trichloromethane to the supernatant, vortex, and centrifuge at 12,000 rpm for 10 min. Collect the supernatant, add 500 µL isopropanol to precipitate RNA, centrifuge at 12,000 rpm for 10 min, wash the precipitates with 70% ethanol, dry under vacuum, and dissolve it in 20-50 µL $H_2O$ (RNase free).

Dilute the RNA with a proper amount of RNase-Free water, and measure the UV absorption values at a wavelength between 200 nm-300 nm. Concentration of RNA=40 µg/ml×A260×dilution factor.

Use RT-PCR to detect the gene expression levels of the midgut RNA samples. Reverse transcription uses RNA PCR Kit (Takara). Reaction system is performed as described in the instructions for the kit. Add 1 µg total RNA into a 20 µl reaction system, and allow it to react for 40 minutes at 42° C. to synthesize the first strand. PCR reaction system is as follows: 2 µL 10× buffer, 0.5 µL 10 mM dNTP, 1 µL primerF, 1 L primerR, 0.5 µL cDNA, 0.2 µL ExTaq enzyme, and add a proper amount of water to make the volume 20 µL. PCR reaction conditions are: 94° C., 4 min; 94° C., 30 s; 55° C., 30 s; 72° C., 30 s; 30 cycles, followed with 72° C., 10 min. The products of PCR are assessed with electrophoresis. Sequences of primer F and primer R that correspond to each gene are shown in table 3.

2. Effect of the Expression of Transgenic Plants' dsRNA on the Growth of *Helicoverpa armigera* and *Ostrinia furnacalis*

Take nearly identically grown 3-instar *H. armigera* larvae (6 *Helicoverpa armigeras* in each group in triplicate for a total of 18 *Helicoverpa armigeras*) and separately feed them non-transgenic WT *Arabidopsis thaliana*, or transgenic *Arabidopsis thaliana* transfected with dstrypsin/2301, dsdopa/2301, dsNADH/2301, dsATP synthase beta/2301 or dsMyosin heavy chain/2301. After 3-7 days, weigh them, calculate the increased weights, and take the average increases as Y-axis values. Assess the weight increases of *Helicoverpa armigera*, and dissect them to collect the midguts. Prepare RNA using the method described in Example 1 and use RT-PCR to assess the expression of the corresponding genes. The results show that transcription of NADH dehydrogenase ubiquinone flavoprotein 2 gene in the midguts of *Helicoverpa armigera* feeding on dsNADH dehydrogenase ubiquinone flavoprotein 2 ubiquinone flavoprotein 2-2 (dsWXM-12 line 2; 12-2) and dsNADH dehydrogenase ubiquinone flavoprotein 2 ubiquinone flavoprotein 2-18 (dsWXM-12 line 18; 12-18) transgenic *Arabidopsis thaliana* is inhibited, as compared to *Helicoverpa armigera* (control) feeding on the wild-type *Arabidopsis thaliana*, and their growths are slower, see FIGS. 4A to 4E, FIGS. 5A to 5C. *Helicoverpa armigera* feeding on ds trypsin precursor-4 (dsWXM-2 line 4; 2-4), ds dopa decarboxylase-2 (dsWXM-6 line 2; 6-2), ds ATP synthase beta-2 (dsWXM-25 line 2; 25-2), and ds Myosin heavy chain-2 (dsWXM-E line 2; E-2) transgenic *Arabidopsis thaliana* grow more slowly, as compared to those (control) feeding on the wild-type *Arabidopsis thaliana*, see FIGS. 4A to 4E, FIGS. 5A to 5C.

Figure 6A:
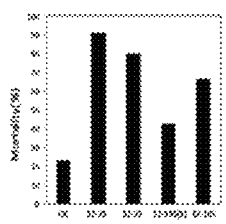
FIGS. 6A to 6E show mortality and body weight changes of *H. armigera* and *Ostrinia furnacalis* after feeding on transgenic cotton expressing dsWXM-12 (dsWXM-12/2301) and VIGS tobacco expressing dsWXM-12, dsWXM-12 (501) or dsWXM-corn dsRNAs.
Figure 6B:
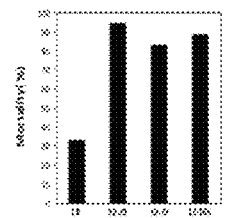

Take nearly identically grown 2-instar *H. armigera* larvae (6 *Helicoverpa* armigeras in each group in triplicate for a total of 18 *Helicoverpa* armigeras) and feed them separately non-transgenic cotton R15 (CK) or dswxm-12/2301 transgenic cotton for 5 days. Then, count the death rates. Perform these experiments independently twice. The results are show in FIGS. 6A and 6B. It can be seen that after feeding on dswxm-12/2301 for 5 days, the mortality of *Helicoverpa armigera* feeding on the transgenic cotton is significantly higher than that of the control feeding on non-transgenic cotton materials (ck).

Figure 6C:
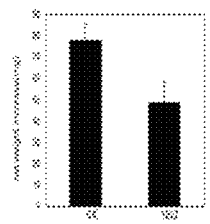
Figure 6D:
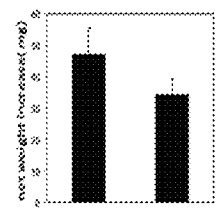
Figure 6E:
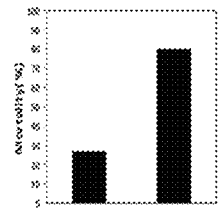
Figure 7A:
FIGS. 7A and 7B show expression of NADH dehydrogenase ubiquinone flavoprotein 2 gene in *H. armigera* mid-gut after feeding on VIGS tobacco plants expressing dsWXM-12 or dsWXM-12(501).
Figure 7B:
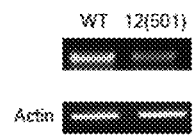

Take nearly identically grown 3-instar *H. armigera* larvae (6 *Helicoverpa armigeras* in each group in triplicate for a total of 18 *Helicoverpa* armigeras) and separately feed them the non-transgenic WT tobacco, or transgenic VIGS tobacco infected with dswxm-12/TRV2 virus, or transgenic VIGS tobacco infected with dswxm-12(501)/TRV2 virus for 5 days. Weigh them and calculate the increased weights. Take the average increases as Y-axis values. The results show that weight increase rates of *Helicoverpa armigera* feeding on tobacco infected with virus dswxm-12/TRV2 or dswxm-12 (501)/TRV2 are slower than that feeding on the wild-type one (as show in FIGS. 6C and 6D). Dissect them to collect the midguts, extract RNA according to the method in Example 1, and perform RT-PCR to assess the expression of the corresponding genes. The results show that transcription of NADH dehydrogenase ubiquinone flavoprotein 2 gene in midguts of *Helicoverpa armigera* feeding on tobacco leaves transfected with dswxm-12/TRV2 or dswxm-12(501)/TRV2 for 3 days is significantly lower than that of insects feeding on the wild type (FIGS. 7A and 7B). These results show that transfecting dsRNA that can lower the transcription of *Helicoverpa armigera*'s NADH dehydrogenase ubiquinone flavoprotein 2 gene into tobacco can improve *Helicoverpa armigera* resistance in the plants. Similarly, it can be expected that the transfection of other molecules that can inhibit the transcription of NADH dehydrogenase ubiquinone flavoprotein 2 gene in *Helicoverpa armigera* may also improve *Helicoverpa armigera* resistance in tobacco.

Take nearly identically grown 2-instar *O. furnacalis* larvae (6 in each group in triplicate for a total of 18 *Ostrinia furnacalis*) and separately feed them non-transgenic WT tobacco, or transgenic tobacco infected with dswxm-corn/TRV2 (NADH dehydrogenase ubiquinone flavoprotein 2 homologous gene in *Ostrinia furnacalis*). After 3 days, count the death rates. The mortality of *Ostrinia furnacalis* feeding on VIGS tobacco transfected with dswxm-corn/TRV2 are significantly higher than those of the control feeding on non-transgenic VIGS tobacco control. Dissect them to collect midguts, extract RNA according to the method in Example 1, and perform RT-PCR to assess the expression of the NADH dehydrogenase ubiquinone flavoprotein 2 gene in the midguts of *Ostrinia furnacalis*. The results show that transcription of NADH dehydrogenase ubiquinone flavoprotein 2 gene in the midguts of *Ostrinia furnacalis* feeding on leaves of tobacco transfected with dswxm-corn/TRV2 for 3 days is significantly lower, as compared to those feeding on the wild type.

Although all examples of the present invention refer to *Helicoverpa armigera* or *Ostrinia furnacalis*, it should be understood that the invention is not limited to particular insects. The insects can be various phytophagous insects that feed on plants, such as lepidopteron.

All the literatures mentioned herein are incorporated by reference in this application, as if each literature reference had been individually cited. In addition, it should be appreciated that one of ordinary skill in the art can modify or vary the invention after reading the above description. Such variations or equivalents also fall within the scope of the claims of the invention.

The invention claimed is:

1. A method for improving insect resistance in a plant, wherein the method comprises:
   expressing a dsRNA that specifically interferes with expression of a cotton bollworm gene in the plant, wherein the dsRNA comprises a nucleotide sequence that is fully complementary to SEQ ID NO: 3 or to a 100-700 bp nucleotide sequence of SEQ ID NO: 3.

2. The method according to claim 1, wherein the expressing the dsRNA comprises:
   (a) providing a construct that expresses the dsRNA, said construct comprises the following structure:

$Seq_{sense}$-X-$Seq_{antisense}$;

wherein $Seq_{sense}$ is SEQ ID NO:3 or the 100-700 bp nucleotide sequence from SEQ ID NO: 3, $Seq_{sense}$ and $Seq_{antisense}$ are fully complementary to each other; X is an intervening sequence between $Seq_{sense}$ and $Seq_{antisense}$; and said intervening sequence is not complementary with $Seq_{sense}$ and $Seq_{antisense}$; and
   (b) transforming the plant with the construct.

3. The method of claim 2, wherein step (b) comprises:
   (i) providing *Agrobacterium tumefaciens* carrying an expression vector, wherein said expression vector contains said construct;
   (ii) contacting a plant cell, a plant tissue, or a plant organ with the *Agrobacterium tumefaciens*, thereby transfecting said construct into the plant cell, the plant tissue, or the plant organ; and
   (iii) regenerating a plant from the transfected plant cell, the plant tissue or the plant organ.

4. The method according to claim 1, wherein the cotton bollworm gene comprises a polynucleotide having the sequence of SEQ ID NO: 3.

5. A method for preparing an interference molecule that specifically interferes with expression of a cotton bollworm gene, the method comprising:
   obtaining the cotton bollworm gene or a fragment thereof, as an inhibition or silencing target; and
   preparing a dsRNA that specifically interferes with expression of the cotton bollworm gene;
   wherein the dsRNA comprises a nucleotide sequence that is fully complementary to SEQ ID NO: 3 or to a 100-700 bp nucleotide sequence of SEQ ID NO: 3.

6. A construct comprising the following structure:

$Seq_{sense}$-X-$Seq_{antisense}$;

wherein $Seq_{sense}$ is a sequence located at nucleotide positions 297-771 of SEQ ID NO: 3, or a sequence located at nucleotide positions 501-899 of SEQ ID NO: 3, and wherein $Seq_{sense}$ and $Seq_{antisense}$ are fully complementary to each other;
   X is an intervening sequence between $Seq_{sense}$ and $Seq_{antisense}$; and said intervening sequence is not complementary with $Seq_{sense}$ and $Seq_{antisense}$.

7. A method for increasing insect resistance of a plant, comprising introducing the construct of claim 6 into the plant.

8. The method according to claim 1, wherein the dsRNA comprises a nucleotide sequence that is fully complementary to a nucleotide sequence selected from SEQ ID NO: 3, to a sequence located at nucleotide positions 297-771 of SEQ ID NO: 3, or to a sequence located at nucleotide positions 501-899 of SEQ ID NO: 3.

9. The method according to claim 5, wherein the dsRNA comprises a nucleotide sequence that is fully complementary to a nucleotide sequence selected from SEQ ID NO: 3, to a sequence located at nucleotide positions 297-771 of SEQ ID NO: 3, or to a sequence located at nucleotide positions 501-899 of SEQ ID NO: 3.

* * * * *